United States Patent

Uchiyama et al.

[11] Patent Number: 5,178,135
[45] Date of Patent: Jan. 12, 1993

[54] THERAPEUTICAL APPARATUS OF EXTRACORPOREAL TYPE

[75] Inventors: Naoki Uchiyama; Takashi Tsukaya; Kouichiro Ishihara; Sakae Takehana; Tetsumaru Kubota; Syuichi Takayama; Akira Taniguchi; Nobuhiko Watanabe; Naomi Sekino; Hiroki Hibino; Masaaki Hayashi, all of Hachioji, Japan

[73] Assignee: Olympus Optical Co., Ltd., Japan

[21] Appl. No.: 755,190

[22] Filed: Sep. 5, 1991

Related U.S. Application Data

[62] Division of Ser. No. 639,922, Jan. 9, 1991, Pat. No. 5,065,741, which is a division of Ser. No. 182,785, Apr. 18, 1988, Pat. No. 4,984,575.

[30] Foreign Application Priority Data

| Apr. 16, 1987 | [JP] | Japan | 62-94870 |
| Apr. 17, 1987 | [JP] | Japan | 62-94583 |
| Apr. 25, 1987 | [JP] | Japan | 62-102809 |
| Apr. 27, 1987 | [JP] | Japan | 62-102071 |
| Apr. 28, 1987 | [JP] | Japan | 62-105637 |
| May 20, 1987 | [JP] | Japan | 62-124838 |
| Jun. 18, 1987 | [JP] | Japan | 62-152777 |
| Jun. 19, 1987 | [JP] | Japan | 62-153163 |
| Jun. 22, 1987 | [JP] | Japan | 62-155749 |

[51] Int. Cl.[5] ............................. A61B 17/22
[52] U.S. Cl. ............................. 128/240 EL; 128/660.03
[58] Field of Search ................. 128/660.03, 24 EL; 606/127, 128

[56] References Cited

U.S. PATENT DOCUMENTS

| 2,947,889 | 8/1960 | Rich . | |
| 3,517,665 | 6/1970 | Sheldon . | |
| 3,772,538 | 11/1973 | Supitilov . | |
| 4,169,984 | 10/1979 | Parisi . | |
| 4,526,168 | 7/1983 | Hassler | 128/24 EL |
| 4,617,931 | 10/1986 | Dory . | |
| 4,634,420 | 1/1987 | Spinosa et al. . | |
| 4,669,483 | 6/1987 | Hepp et al. . | |
| 4,763,652 | 8/1988 | Brisson | 128/24 EL |
| 4,771,787 | 9/1988 | Wurster et al. . | |
| 4,796,613 | 1/1989 | Heumann et al. . | |
| 4,803,445 | 2/1989 | Ishida et al. | 128/660.03 |
| 4,821,729 | 4/1989 | Makofski et al. . | |
| 4,836,191 | 6/1989 | Noske et al. . | |
| 4,861,332 | 8/1989 | Parisi . | |
| 4,886,060 | 12/1989 | Wiksell . | |
| 4,958,639 | 9/1990 | Uchiyama et al. | 128/660.03 |

Primary Examiner—Kyle L. Howell
Assistant Examiner—Scott R. Akers
Attorney, Agent, or Firm—Ostrolenk, Faber, Gerb & Soffen

[57] ABSTRACT

A therapeutical apparatus includes a measuring apparatus including a probe which generates an X-ray or ultrasonic wave in order to detect the location of a target to be treated such as calculi situated within the kidney, liver, biliary ducts. A therapeutical energy generator generates a shock wave of sufficient energy for purpose of therapy externally of the physical body and focusses it upon the target. Structure is provided for causing a displacement of the generator and the measuring apparatus around the surface of a patient. Structure is provided to activate the generator.

3 Claims, 27 Drawing Sheets

FIG. 8
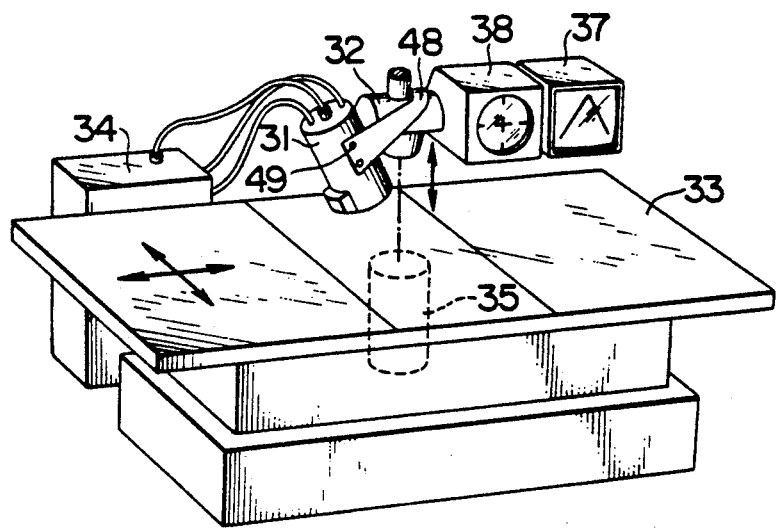
FIG. 9
FIG. 10
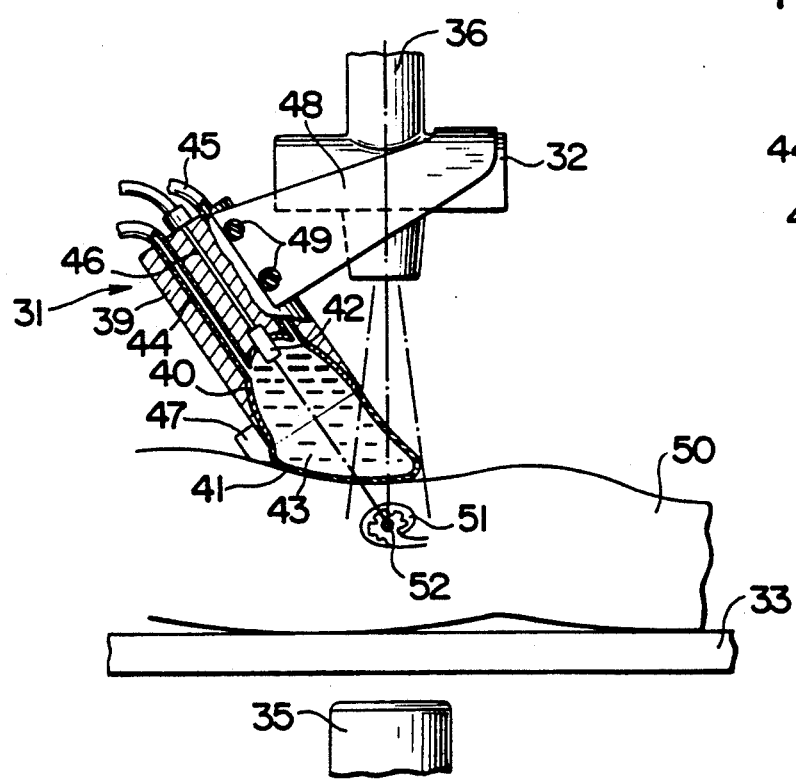

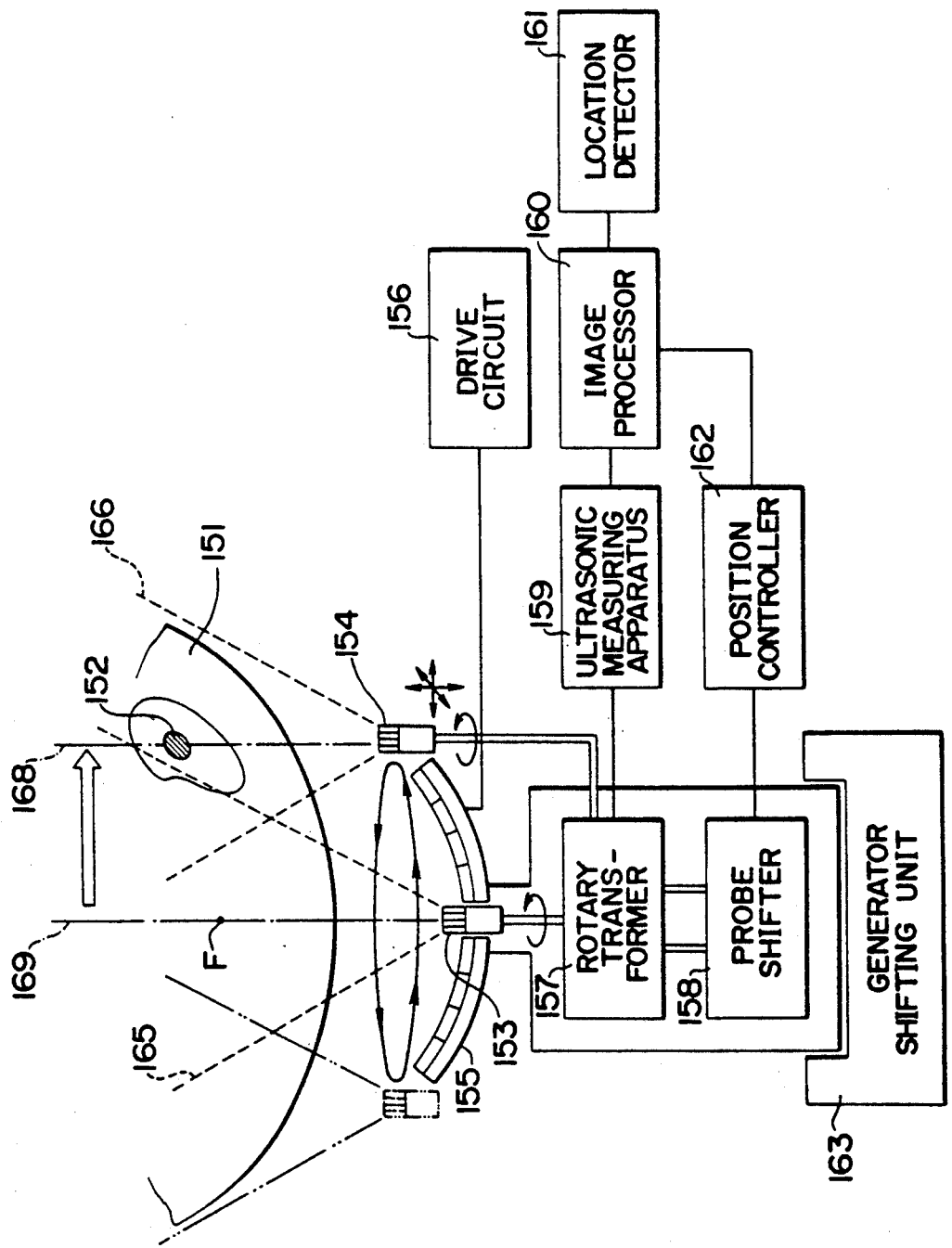

THERAPEUTICAL APPARATUS OF EXTRACORPOREAL TYPE

This is a division of application Ser. No. 07/639,922, filed Jan. 9, 1991, now U.S. Pat. No. 5,065,741 which is a division of U.S. Ser. No. 182,785 now U.S. Pat. No. 4,984,575, issued Jan. 15, 1991.

FIELD OF THE INVENTION AND RELATED ART STATEMENT

The invention relates to a therapeutical apparatus of extracorporeal type, and more particularly, to a therapeutical apparatus of extracorporeal type in which an object to be treated such as a calculus formed within a physical body of a patient is detected by a measuring apparatus, and a therapeutic energy of shock wave which is generated externally of the physical body is focussed upon the object to fracture it, in particular, to an ultrasonic therapeutical apparatus which focusses an ultrasonic shock wave from a source located externally of the physical body upon an object to be treated such as a calculus for purpose of fracture thereof.

PRIOR ART

An arrangement which utilizes an X-ray or ultrasonic measuring apparatus to detect the presence of a calculus formed in a bile duct or kidney, and which also utilizes therapeutical energy in the form of a shock wave which is produced, as by voltage discharge or ultrasonic vibration, externally of the physical body of a patient and is focussed upon the calculus to fracture it, is disclosed in U.S. Pat. No. 4,617,931. As disclosed in this patent, a probe comprising piezoelectric elements disposed in an array in a mosaic pattern along a quadratic surface is brought into contact with a patient on his back through a water bag filled with an ultrasonic wave transmitting medium such as water interposed therebetween in order to focus an ultrasonic shock wave from the piezoelectric elements upon a calculus as formed within a kidney to fracture it. As disclosed in Japanese Laid-Open Patent Applications No. 31,140/1986 and No. 45,747/1986, an arrangement may be made to enable the ultrasonic probe to move across an extensive area and to focus an ultrasonic wave of increased intensity upon a calculus once it is searched out. Japanese Laid-Open Patent Application No. 37,149/1986 discloses a measuring apparatus including a detection system which determines the positions in two directions. The present applicant has also proposed an arrangement which permits a displacement of the ultrasonic probe in a direction perpendicular to the scan direction, as disclosed in Japanese Patent Application No. 282,979/1986. U.S. Pat. No. 4,526,168 discloses a technique to focus the ultrasonic wave upon the location of a calculus by changing the timing and phases with which a plurality of piezoelectric elements are driven. In the ultrasonic therapeutical apparatus disclosed in U.S. Pat. No. 4,617,931 the ultrasonic probe is located only at the center of an ultrasonic wave generator which provides an ultrasonic wave of an increased intensity, resulting in a limited extent over which an observation is possible and thus causing a disadvantage that the arrangement may fail to locate a calculus. When a displacement of the probe in a direction perpendicular to the scan direction is enabled as disclosed in Japanese Patent Application No. 282,979/1986, a tracking of a movement of the calculus is possible, but it is still difficult to locate the calculus before the therapy is conducted. A manual focussing operation resulted in a low hit rate of the ultrasonic wave whenever the calculus happens to move as a result of breathing operation.

The ultrasonic therapeutical apparatus disclosed in Japanese Laid-Open Patent Application No. 31,140/1986 enables the extent of observation to be extended, but involves a combination with a patient suspension system during his bath in a water vessel, thus disadvantageously requiring a very bulky arrangement. The ultrasonic therapeutical apparatus disclosed in Japanese Laid-Open Patent Application No. 37,149/1986 uses X-ray in its detector, which may be hazardous to the patient. In addition, where a pair of ultrasonic probes are employed, they are disposed such that each scan plane passes through the focus of a reflector of the shock wave and that their axes are perpendicular to each other. This limits the extent of observation which is a vailable, and thus still leaves much to be improved.

An ultrasonic therapeutical apparatus disclosed in U.S. Pat. No. 4,617,931 includes means for positioning the focus of a shock wave at the location of a calculus. Specifically, an ultrasonic wave or X-ray is employed to detect the spatial location of a calculus within the physical body of a patient, as illustrated in FIG. 46, where the focal position of the shock wave is indicated by a marker on an image 300 which is obtained by ultrasonic or X-ray tomography. The positioning is achieved by bringing an image 302 of a calculus into alignment with the marker. Thus, the position of a focus F is indicated as shown at 304 on a display 303, and means for generating a shock wave is moved so that the image 302 of the calculus is aligned with the position of the focus F. However, such technique only indicates the focal position of the display. Accordingly, where an organ such as lung, intestines or bones which are sensitive to the shock wave located around the calculus when the latter is to be fractured, there arises a significant problem that such organ may be damaged or otherwise adversely influenced by the shock wave.

Another form of therapeutical apparatus of extracorporeal type is disclosed in Japanese Patent Application No. 282,980/1986 (see FIGS. 44 and 45). In this instance, the apparatus comprises ultrasonic measuring means 311 (location detecting means) which detects the location of a calculus within the physical body, positioning signal generating means 312, focus shifting means 313 and shock wave generating means 314 which generates a shock wave used to fracture a calculus.

The ultrasonic measuring means 311 comprises an ultrasonic measuring unit 317 which radiates an ultrasonic wave directed toward a patient 315 to detect the location of a calculus 316, and a display unit 318 which receives a detection signal to indicate the location of the calculus on a screen of CRT.

The positioning signal generating means 312 includes a signal generator 320 which fixes a marker on a given point on the screen of the display unit 318 and produces a signal delivered to focus shifting means 313 which is effective to bring the focus of the fracturing shock wave into alignment with the location of the marker. The generator 320 is effective to process the image of the detected calculus so that an operator such as a surgeon is capable of recognizing the size or the number of calculus or calculi displayed and to indicate a most effective signal on the screen as by a light pen to indicate the sequence in which the calculi are sequentially to be fractured in the sequence of the decreasing size where a plurality of calculi are involved, or to indicated a particular region of a coral calculus where the fracture is to be initiated or to change the focal position of the shock wave in response to the detection of the location and the size of the calculus which is performed periodically during the fracturing process because of a displacement of the calculus. The generator stores such signals, and deliver them to a drive unit 319 which shifts the shock wave generator during the fracturing process.

The focus shifting means 319 or the drive unit which shifts the shock wave generator operates to drive both a water bag 321 and a shock wave generator 322 by a numerically controlled robot in accordance with the positioning signal. The shock wave generator 322 comprises a plurality of ultrasonic vibrators or piezoelectric elements 323 which are applied to and secured to the front surface of a mounting plate 324, which is formed as a a spherical surface, in a mosaic pattern. The front surface of the piezoelectric elements which emit the shock wave is directed toward the patient 315. The water bag 321 comprising an ultrasonic wave transmitting medium and including means for injecting liquid medium and controlling the pressure is interposed between the shock wave generator 322 and the patient 315. The shock wave transmitting liquid such as water is filled in the bag 321.

The shock wave generating means 314 comprises an ultrasonic pulse voltage generator which is known in itself, and which is effective to drive the piezoelectric elements 323.

FIG. 45 indicates the sequence of operation performed by the apparatus mentioned above. Initially, the location of the calculus within the physical body of a patient is detected by the measuring means 311. The positioning signal generating means 312 analyzes the condition of the calculus which is detected by the measuring means. An operator such as a surgeon selects an optimum procedure to treat the calculus depending on the kind thereof. In response thereto, a positioning signal which determines the sequence of treatment is stored. The focus shifting means 313 is activated in accordance with the positioning signal to drive the water bag 321 and the shock wave generator 322 so that the shock wave is focussed upon the calculus. Subsequently, a shock wave is generated in response to the shock wave generating means 314 to fracture the calculus. After a given number of shock waves have been generated, the procedure is temporarily stopped, and the size of the remaining calculus or the focal position of the shock wave is determined again, and the above operation is repeated until the calculus is completely fractured.

However, in the therapeutical apparatus of extracorporeal type as mentioned above, the use of the ultrasonic wave for purpose of observing the location of an object such as a calculus and for aiming fails to provide a tomographic image of good quality because of the spacing between the apparatus and the patient, presenting a difficulty in the aiming operation.

In addition, in the apparatus described above, the entire shock wave generator has been moved in order to bring the focal position of the shock wave into alignment with the location of a calculus. However, because the shock wave generator including the water bag is of an increased weight, an extensive unit is required for its movement, still suffering from an insufficient speed of movement.

On the other hand, a calculus or tumor which is to be treated by such ultrasonic therapeutical apparatus tends to move in response to the breathing or a movement of blood vessel, and thus may be displaced from the focal position of the ultrasonic beam. In such instance, the focal position of the ultrasonic beam must be aligned with a region to be treated in order to avoid a wasteful generation of ultrasonic wave. This increases the length of time required for the therapy and also involves a risk that normal tissues may be jeopardized. A movement caused by the breathing may be rapid enough to prevent an automatic tracking of the focal point of the ultrasonic beam with respect to the moving calculus to be prevented since the water bag itself has a given magnitude.

Almost all apparatus of the kind described utilizes a devoted bed on which a patient is positioned in supine posture. The bed includes a table section supporting an upper region of a patient including his shoulder and heat and another table section supporting a lower section extending from the waist to the feet, leaving a free space between the breast and the abdomen. A patient is laid in supine posture on the bed, and the measuring apparatus as well as a unit for generating therapeutical energy are brought close to or into abutment against the patient to perform the treatment. Accordingly, the posture of the patient is limited, having a small degree of freedom during the therapy, which restricts the space requirement for the measuring apparatus and the energy generating apparatus. Specifically, with an X-ray measuring apparatus, it is only possible to cause the X-ray to transmit through the physical body of a patient. With an ultrasonic measuring apparatus, it is only possible to move the ultrasonic vibrator along the surface of the physical body. There has been no capability to provide an efficient, fine adjustment of the angle with which the X-ray transmits or the angle at which the ultrasonic wave is emitted. Considering a therapeutical energy generator, it is incapable of allowing a shock wave generator to be disposed at an angle which avoids the location of a lung for a biliary calculus, and to adjust the angle at which the shock wave is emitted to an efficient angle, it being only possible to guide the shock wave generator along the physical body of a patient.

Usually, a supine posture is chosen for therapy of a biliary calculus while either a supine or prone posture is chosen for a renal calculus, and it is unfavorable that a posture used for the therapy be restricted by a devoted bed.

It will be appreciated that a hospital is usually provided with a X-ray apparatus and an ultrasonic diagnostic apparatus, and therefore it is uneconomical to purchase a therapeutical apparatus of extracorporeal type with a devoted bed anew. It is desirable that a therapeutical apparatus of extracorporeal type be provided which enables a therapy utilizing a common bed which allows a free choice of either supine or prone posture.

Thus, an ordinary hospital is usually provided with an X-ray unit or ultrasonic diagnostic apparatus which may be used as the measuring apparatus mentioned above as well as associated patient beds. If a therapeutical apparatus of extracorporeal type as mentioned above must be provided anew, an increased demand in space requirement and additional cost result.

OBJECT AND SUMMARY OF THE INVENTION

It is a first object of the invention to provide a therapeutical apparatus of extracorporeal type which enables an improvement in the degree of freedom of a therapy posture which improves the economical aspect and which is capable of adjusting an angle with which a measuring apparatus makes an observation as well as an angle with which energy from a therapeutical energy generator is emitted or directed.

It is a second object of the invention to provide a therapeutical apparatus of extracorporeal type which improves the space requirement and the cost required by eliminating unnecessary demand while utilizing an ultrasonic diagnostic apparatus or X-ray unit which is usually provided in an ordinary hospital as a measuring apparatus of the therapeutical apparatus.

It is a third object of the invention to eliminate disadvantages of the prior art, by providing an ultrasonic therapeutical apparatus having enhanced coverage of measuring while facilitating the capture of a calculus location before the therapy and also enabling an accurate tracking of the calculus location for efficient therapy.

It is a fourth object of the invention to provide a therapeutical apparatus of extracorporeal type which is capable of detecting a movement of a calculus to bring a focus into alignment with the location of the calculus which has moved in a quick manner, thus realizing an efficient and dependable therapy.

It is a fifth object of the invention to provide a therapeutical apparatus of extracorporeal type which is capable of reliably bringing the focal position of a shock wave into alignment with a recognized calculus in an accurate manner while avoiding adverse influences upon other organs, thus further improving the fracture efficiency and reducing the length of time required for the therapy while avoiding any pains to the patient.

It is a sixth object of the invention to provide an ultrasonic probe having a simplified construction and exhibiting an increased efficiency. In accordance with the invention, any posture may be utilized for the therapy. A fine adjustment of the angle at which an observation is made as well as the angle at which the shock wave used for the therapy is emitted to achieve a most efficient operation is enabled. The apparatus of the invention may be used in combination with any other instrument such as X-ray unit in a facilitated manner, thus avoiding unnecessary economical load and minimizing the space requirement while improving the degree of freedom and the economical advantage.

In accordance with the invention, an ultrasonic shock wave is radiated in recognition of the location within a specified area (an area of interest-AOI) where a calculus exists, thus eliminating a wasteful emission of ultrasonic shock wave to provide a further enhanced therapy efficiency.

In accordance with the invention, the use of an ultrasonic probe allows an increased coverage for observation, facilitating the capture of the location of a calculus before it is treated. In this manner, any resort to a separate ultrasonic observation unit as has been done conventionally is avoided. The capture and the automatic tracking of a calculus enable the length of time required for the therapy to be reduced and any pain caused to the patient to be diminished, because an efficient treatment is achieved.

In accordance with the invention, the focal position of an ultrasonic shock wave may be brought into alignment with any object being treated which may move rapidly as a result of a breathing operation, by merely choosing ultrasonic vibrators which are to be driven while maintaining a shock wave generator at a fixed position. The focal position is brought into alignment with the object by an electronic technique which utilizes CPU to drive a drive circuit, and hence the arrangement is compact in construction and is efficient in achieving the therapy of an object such as a calculus.

Additionally, if a calculus or tumor changes its position as a result of a breathing operation of a patient, the ultrasonic wave may be maintained in focus with such object being treated, thus improving the efficiency of the therapy and enhancing the safety of the therapy by avoiding the concentration of an ultrasonic wave upon areas which are unrelated. This is achieved by feeding a digital signal representing the location of a calculus or tumor detected by the ultrasonic probe to CPU, which then operates to provide an automatic control for focussing the ultrasonic wave in focus with an area to be treated, thus avoiding manual intervention and allowing an automatic tracking.

Additionally, in accordance with the invention, an image representing a spatial location of a focus within the physical body of a patient may be obtained by driving ultrasonic vibrators. Data representing the distribution of the intensity of the ultrasonic wave which is previously calculated is superimposed upon the image to provide a color display, whereby the location of the calculus may be readily and reliably positioned to a point where the intensity of the shock wave is at its maximum. This also allows a decision to see if any organ such as lung, intestine or bones which are sensitive to the shock wave is located within a region where the intensity of the shock wave is significant. In this manner, any damage to such organ may be avoided by changing the posture of the patient or by moving the shock wave generator.

BRIEF DESCRIPTION OF THE DRAWINGS

FIG. 8 is a perspective view of a therapeutical apparatus of extracorporeal type according to a third embodiment of their invention;

FIG. 9 is a fragmentary, longitudinal section, to an enlarged scale, illustrating one manner of use of the apparatus shown in FIG. 8;

FIG. 10 is a longitudinal section of a water bag in its shrunk condition;

FIG. 26A being a cross section illustrating the relationship between an acoustical prism and a focal position.

FIG. 27 is a schematic illustration of an ultrasonic therapeutical apparatus according to a fourteenth embodiment of the invention;

DETAILED DESCRIPTION OF PREFERRED EMBODIMENTS

Figure 1:
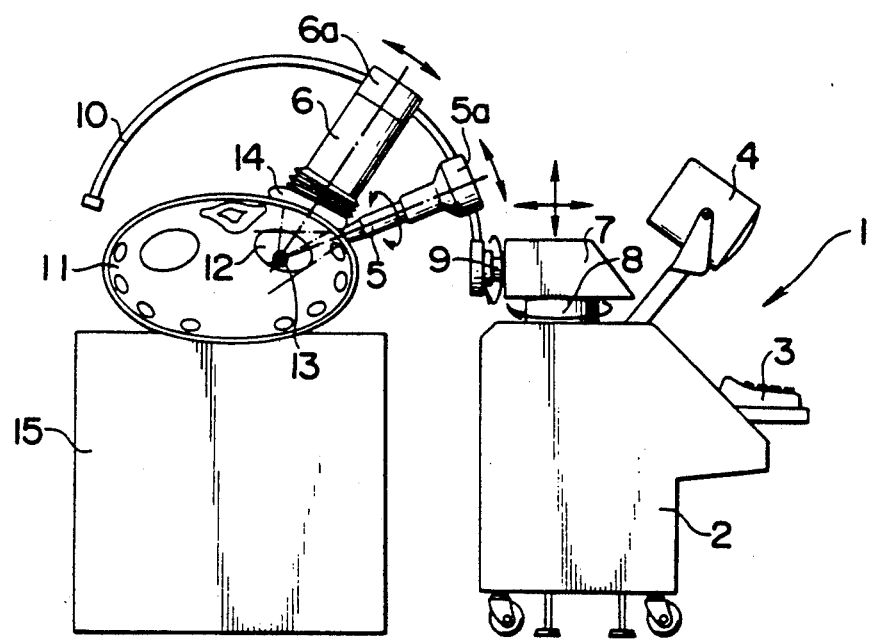
FIG. 1 is a side elevation of a therapeutical apparatus of extracorporeal type according to a first embodiment of the invention.

Referring to the drawings, the invention will now be described with reference to several embodiments thereof. In the description to follow, a therapeutical apparatus of extracorporeal type is constructed as a calculus fracture apparatus, but is should be understood that the apparatus of the invention is not limited in its application to the fracture of a calculus.

FIG. 1 shows a therapeutical apparatus 1 of extracorporeal type according to a first embodiment of the invention, including a movable body 2 on which an operating keyboard 3 and a monitor display 4 are installed and also carrying an operating head 7 which guides a measuring apparatus 5 and a therapeutical energy generator 6 to a desired angular position.

The head 7 is mounted on the top end of a rotatable shaft 8 which is vertically supported within the body 2. The shaft 8 can be elevated up and down to permit a vertical movement of the head 7, which is also movable toward and away from a patient 11 by a mechanism, not shown. The head 7 carries a support shaft 9 which projects horizontally and forwardly, with a guide arm 10 mounted on the free end of the support shaft 9. The measuring apparatus 5 is slidably mounted on the arm 10 by means of a movable mount 5a, and the energy generator 6 is also slidably mounted on the arm 10 by a movable mount 6a. The guide arm 10 is arcuate in configuration, or semi-circular in the present embodiment so that both the measuring apparatus 5 and the generator 6 may be moved around one-half the circumference of the patient 11. The support shaft 9 is also rotatable around its axis, whereby the guide arm 10 is rotatable through 360° around an extension of the axis of the support shaft 9.

The measuring apparatus 5 mounted on the movable mount 5a includes an ultrasonic vibrator which performs a sector scan, for example, radiating an ultrasonic wave toward the patient 11 to detect the location of a calculus 13 which may be located within a kidney 12 of the patient. The detected renal calculus 13 is displayed on the screen of the monitor display 4 which may comprise a cathode ray tube.

The therapeutical energy generator 6 mounted on the movable mount 6a includes a source of high tension discharge type for generating a shock wave energy, which is then focussed upon the renal calculus 13 within the patient 11, through an interposed water bag 14 such as Goatex (trademark) which is filled with a shock wave transmitting medium such as water, for fracturing the calculus 13.

Figure 2:
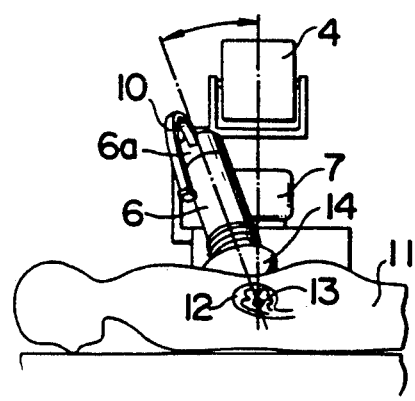
FIGS. 2 and 3 are a fragmentary rear view and a side elevation, illustrating manners of operating the apparatus shown in FIG. 1.
Figure 3:
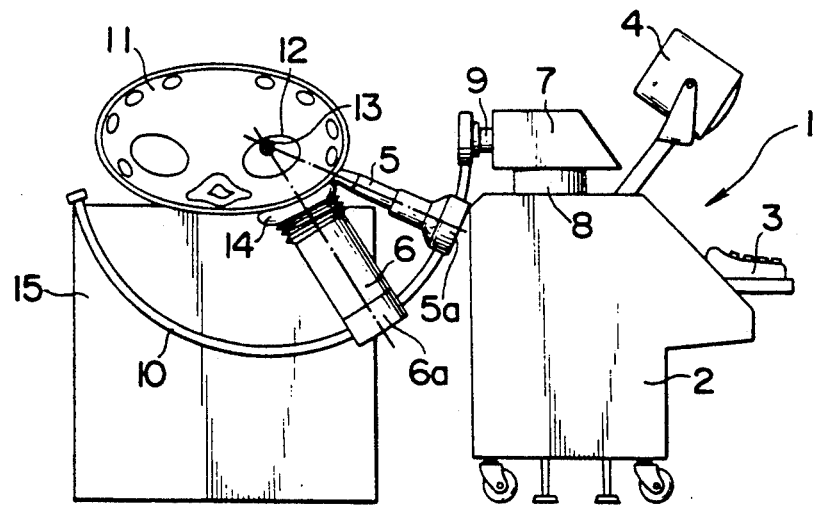

In operation, the patient 11 usually lies on an ordinary bed 15 in prone posture, and the body 2 is moved close to the patient. By adjusting the operating head 7 back and forth and vertically up and down, the guide arm 10 is brought in spaced, opposing relationship with the circumference of the patient 11 so as to facilitate a detection and a fracture of the calculus by bringing the measuring apparatus 5 and the energy generator 6 close to or in abutment against the surface of the patient. As illustrated in FIG. 2, when the fracture is to be conducted, the support shaft 9 may be rotated around its axis to bring the guide arm 10 to an inclined position with respect to the surface of the patient so that the generator 6 may be brought to an angular position which provide a maximum fracture efficiency or where the location of a lung or the like may be avoided from the path of radiation of the shock wave energy.

Where the patient 11 lies on the bed 15 in supine posture as illustrtated in FIG. 3, the support shaft 9 may be rotated through 180° to position the guide arm 10 in the space below the bed 15, whereby the measuring apparatus 5 and the generator 6 are brought close to or into abutment against the patient 11 from the underside thereof for therapy.

Figure 4:
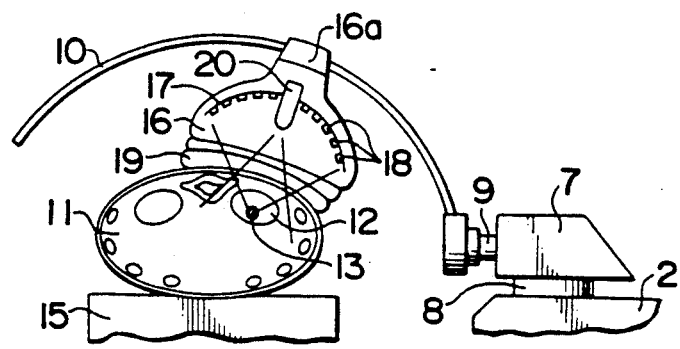
FIG. 4 is a schematic view of a therapeutical apparatus according to a second embodiment of the invention.

FIG. 4 is a schematic illustration of a therapeutical apparatus of extracorporeal type according to a second embodiment of the invention. The apparatus shown in this Figure differs from the first embodiment in that the energy generator 6 comprises an ultrasonic shock wave generator 16. Specifically, the generator 16 comprises a mounting plate 17 in the form of a spherical shell, on the internal surface of which a multiplicity of ultrasonic vibrators 18, formed by piezoelectric elements, are secured in a mosaic pattern so that their front surface on which a shock wave is generated faces the patient 11. A water bag 19 of a material such as Goatex (trademark) which includes liquid injection means and pressure control means is interposed between the generator and the patient 11. The bag 19 is filled with a shock wave transmitting liquid such as water. An ultrasonic measuring apparatus 20 which is adapted for a linear scan or a sector scan is mounted centrally on the mounting plate 17.

The ultrasonic energy generator 16 is a movably mounted on the guide arm 10 by means of a movable mount 16a. In other respects, the arrangement is similar to the first embodiment, and this embodiment operates in a similar manner with a similar effect as in the first embodiment.

Figure 5:
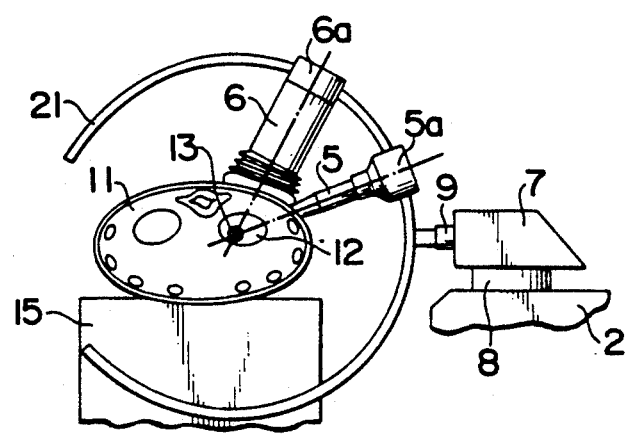
FIG. 5 is a side elevation of another form of guide arm.

In FIG. 5, the guide arm 10 of the first embodiment is replaced by a C-ring shaped guide arm 21 on which the measuring apparatus 5 and the therapeutical energy generator 6 may be movably mounted, again facilitating the operation when the posture of the patient is changed for purpose of the therapy. This also allows the utilization of an X-ray unit having a C-shaped guide arm as the measuring apparatus associated with the therapeutical apparatus of the invention.

Figure 6:
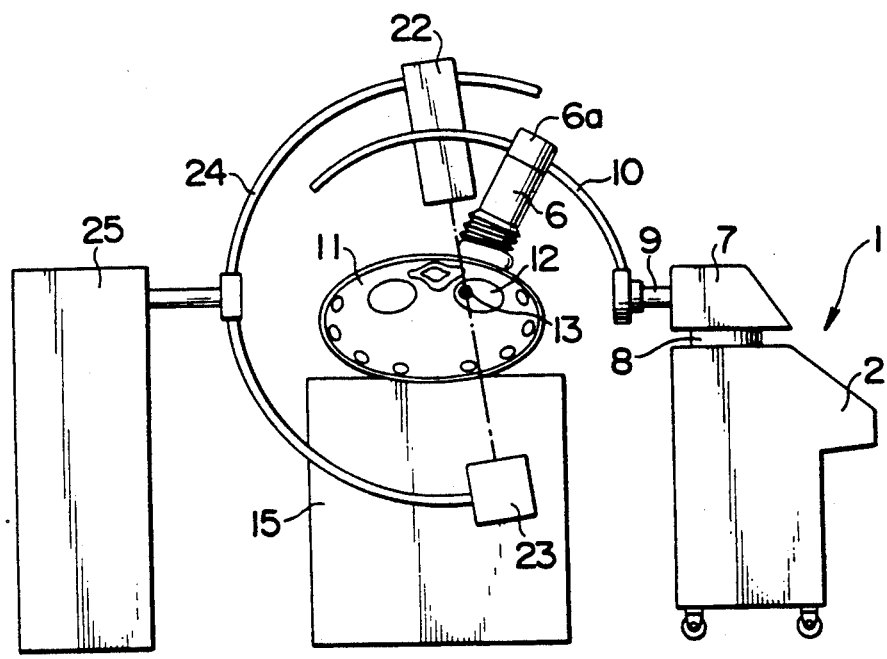
FIG. 6 is a side elevation of a therapeutical apparatus according to the invention is combination with an X-ray unit.

Specifically, as shown in FIG. 6, an X-ray unit 25 carries a C-shaped guide arm 24 on which an X-ray emitter 22 and an image intensifier 23 which is an X-ray receptor and comprising photomultipliers are mounted in opposing relationship relative to each other. The unit 25 may be disposed along one side of the patient 11 lying on the bed 15 while the therapeutical apparatus 1 including either the therapeutical energy generator 6 or 16 mounted on the guide arm 10 may be disposed on the other side. In this manner, the location of the calculus 13 may be detected by the X-ray observation unit 25, and then the therapeutical apparatus 1 may be activated to fracture the calculus 13.

Figure 7:
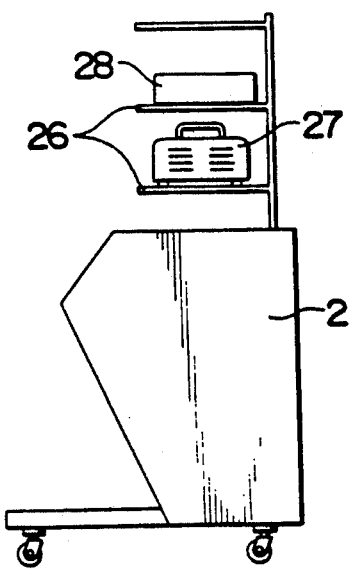
FIG. 7 is a side elevation of another form of the therapeutical apparatus.

The therapeutical apparatus of the invention may be used in combination with an endoscope. As illustrated in FIG. 7, the body 2 of the therapeutical apparatus may be provided with shelves 26 on which a light source unit 27 for the endoscope and a treatment tool 28 may be disposed for convenience of the operation.

FIGS. 8 to 10 shows a third embodiment of the invention which utilizes an X-ray unit which is usually provided in an ordinary hospital as the measuring apparatus for the therapeutical apparatus of the invention. Specifically, the X-ray unit includes an X-ray emitter 32 on which a therapeutical energy generator 31 is mounted in a detachable manner. The emitter 32 is disposed to be movable up and down above a surgical bed 33 and has an arm-shaped mounting member 48 secured thereto which extends at an angle downwardly. The generator 31 is detachably mounted on the mounting member 48 by mounting screws 49. The generator 31 is of a high tension discharge type and includes an external housing 39 having a focussing reflector 40 disposed in its free end which comprises an elliptical curved surface. A discharge electrode 42 is located at one of foci of the elliptical surface, and the opening of the reflector 40 is covered by a flexible water bag 41 which is filled with a shock wave transmitting medium 43 such as water, thus filling the space between the external surface of a patient 50 and the discharge electrode 42. A pair of pipings 44, 45 are disposed inside the housing 39 to supply or discharge water to and from the bag 41. The electrode 42 is connected through a connection cord 46 passing through the housing 39 to a source of high tension 34, whereby a discharge voltage may be applied to the electrode. An ultrasonic probe 47 which is used as an auxiliary measuring apparatus is disposed along the underside of the housing 39.

The X-ray emitter 32 is supported by a support member 36 to be movable vertically above the surgical bed 33 which is horizontally translatable in two perpendicular directions as is well known, and the X-ray which is emitted transmits through the patient 50 lying on the bed to be received by an X-ray recepter or an image intensifier 35 comprising photomultipliers which is disposed in opposing relationship with the X-ray emitter 32 below the bed 33. The arrangement may include a monitor 37 which indicates the focus of the shock wave and an X-ray monitor 38. A kidney of the patient 50 is shown at 51, with a calculus 52 located therein.

In operation, when the energy generator 31 is mounted on the X-ray measuring apparatus, both the apparatus are adjusted so that the axes of ultrasonic energy as well as the X-ray radiation intersect each other at the location of an affected part of the patient 50, for example, calculus 52, as indicated in FIG. 9. The apparatus is connected to the source 34 as well as a source of water, not shown, which is connected through the pipings 44, 45. The patient 50 then lies on the bed 33. The X-ray unit is then operated to cause the X-ray to pass through the kidney 51 thereof, thus observing and detecting the calculus 52. At this time, it is desirable that the water bag 41 be held shrunk as indicated in FIG. 10 to approach the opening of the reflector 40, by discharging the water therefrom, in order to prevent its interference with the observation by the X-ray unit. After the calculus 52 is detected, the water is supplied to the water bag 41 to expand it, and the support member 36 is operated to bring it into close contact with the surface of the patient. While observing the monitor 37, the location of the calculus 52 is brought to the other focal position of the elliptical reflector 40. A high tension is then applied to the electrode 42 to cause its discharge, whereupon shock wave energy is focussed upon the calculus 52 located within the kidney 51, thus fracturing it as intended to allow it to be egested in a natural manner.

As described, while the therapeutical apparatus of the invention may be used in combination with an X-ray unit to detect the location of a calculus, it should be understood that the location of a calculus may also be detected by an ultrasonic probe 47 mounted on a housing 39. In addition, the therapeutical energy generator 31 may be detachably mounted on the image intensifier 35 of the X-ray unit with a similar effect.

Figure 11:
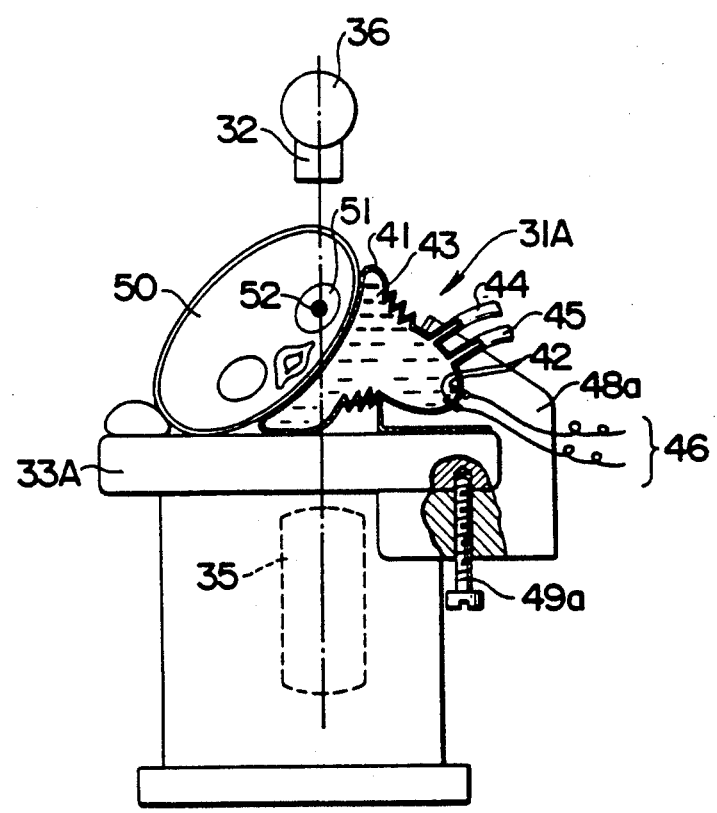
FIG. 11 is a schematic view, partly in longitudinal section, of a therapeutical apparatus of extracorporeal type according to a fourth embodiment of the invention.

FIG. 11 is a longitudinal section of a therapeutical apparatus of extracorporeal type according to a forth embodiment of the invention, which is similar to the apparatus shown in FIGS. 8 and 9. Accordingly, similar parts are designated by corresponding numerals without repeating their description. Specifically, the only difference lies in the fact that a therapeutical energy generator 31A is detachably mounted on the surgical bed in distinction to the energy generator 31 which is detachably mounted on the X-ray emitter 32 or the image intensifiers 35 in the embodiment of FIGS. 8 and 9. Thus, referring to FIG. 11, the generator 31A is detachably mounted on a surgical bed 33A by mounting screws 49A with a mounting member 48A interposed therebetween. When the energy generator is directly mounted on the bed 33A, the generator 31A may be more firmly secured to improve the stability during its use. The apparatus functions in the similar manner and achieve the similar effect as the therapeutical apparatus shown in FIGS. 8 and 9.

Figure 12:
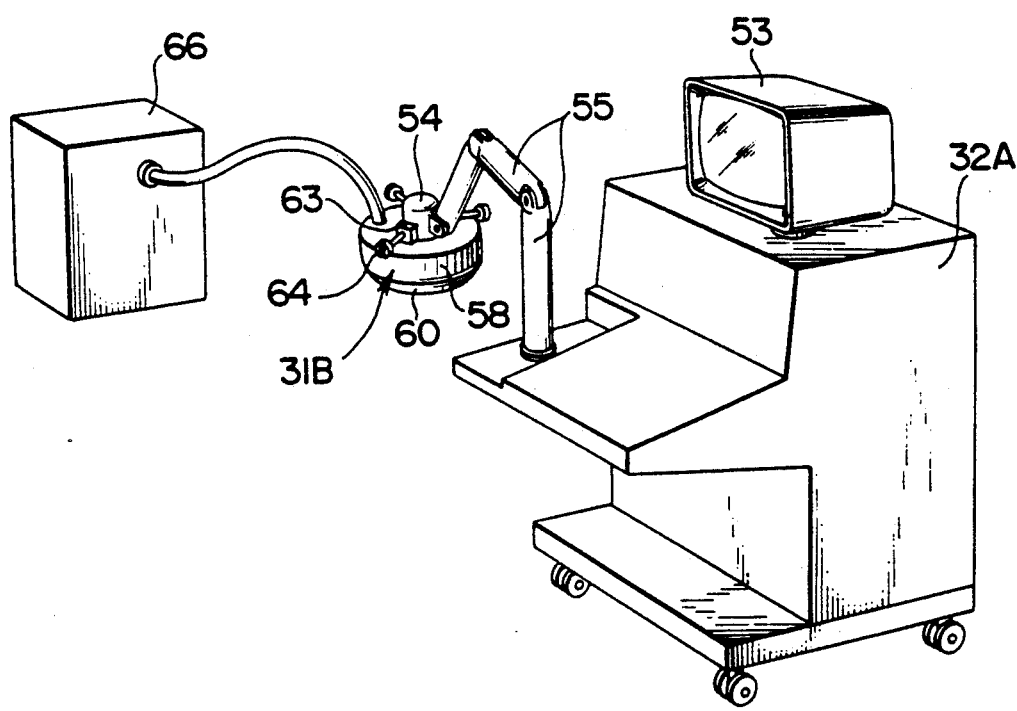
FIG. 12 is a perspective view of a therapeutical apparatus of extracorporeal type according to a fifth embodiment of the invention.

FIG. 12 is a schematic illustration of a therapeutical apparatus of extracorporeal type according to a fifth embodiment of the invention which is used in combination with an existing ultrasonic diagnostic apparatus utilized as a measuring apparatus, with a therapeutical energy generator detachably mounted thereon. Specifically, FIG. 12 shows a therapeutical energy generator 31B, an ultrasonic diagnostic observation apparatus 32A, an observation monitor 53, an ultrasonic probe of mechanical scan type associated with the apparatus 32A, and an arm 55 which carries the probe 54 in a movable manner. As shown, the ultrasonic diagnostic apparatus 32A is free to move about, and the probe 54 may be freely positioned relative to an affected part 57 of a patient 56 (see FIG. 13) by means of the arm 56.

Figure 13:
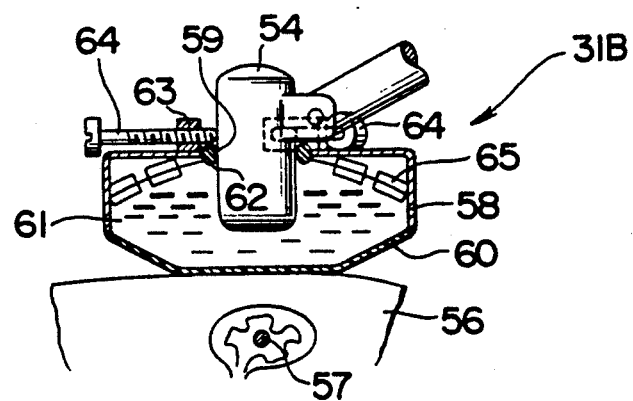
FIG. 13 is a fragmentary cross section, to an enlarged scale, of the apparatus shown in FIG. 12.

Referring to FIG. 13, the therapeutical energy generator 31B comprises a body 58 in the form of a cup-shaped casing having an opening 59 centrally in its top in which the probe 54 is fitted and having a bottom opening which is closed by a water bag 60. An array of piezoelectric elements 65 is disposed along a spherical surface on the internal ceiling surface of the body 58. The water bag 60 is filled with water 51 acting as an ultrasonic wave transmitting medium, and an O-ring 62 is fitted around the top opening 59 to maintain the body 58 water-tight against the probe 54. The top of the body 58 is integrally formed with three threaded lugs 63, which are engaged by mounting screws 64 to permit the apparatus 31B to be detachably mounted on the probe 54 of the ultrasonic diagnostic apparatus 32A. The piezoelectric elements 65 are connected to a drive unit 66, and shock wave energy generated by the piezoelectric elements 65 is focused upon the affected part 57 such as the calculus of the patient 56 for fracturing it.

In use, the therapeutical energy generator 31B is mounted on the probe 54 of the ultrasonic diagnostic apparatus 32A by means of the mounting screws 64, and piezoelectric elements are connected to the drive unit 66. The generator 31B is located relative to the affected part 57 of the patient 56 with the surface of the water bag 60 disposed in close contact therewith as illustrated in FIG. 13. The probe 54 is utilized to detect the affected part such as a calculus, and then the affected part 57 is brought to the focal position of the array of piezoelectric elements. A drive voltage is then applied to the piezoelectric elements 65 from the drive unit 66 to generate a shock wave, which is focussed upon the affected part 57 to fracture it. In this manner, the apparatus of the present embodiment operates in the similar manner and achieves a similar effect as the apparatus of the third and the fourth embodiment.

Figure 14:
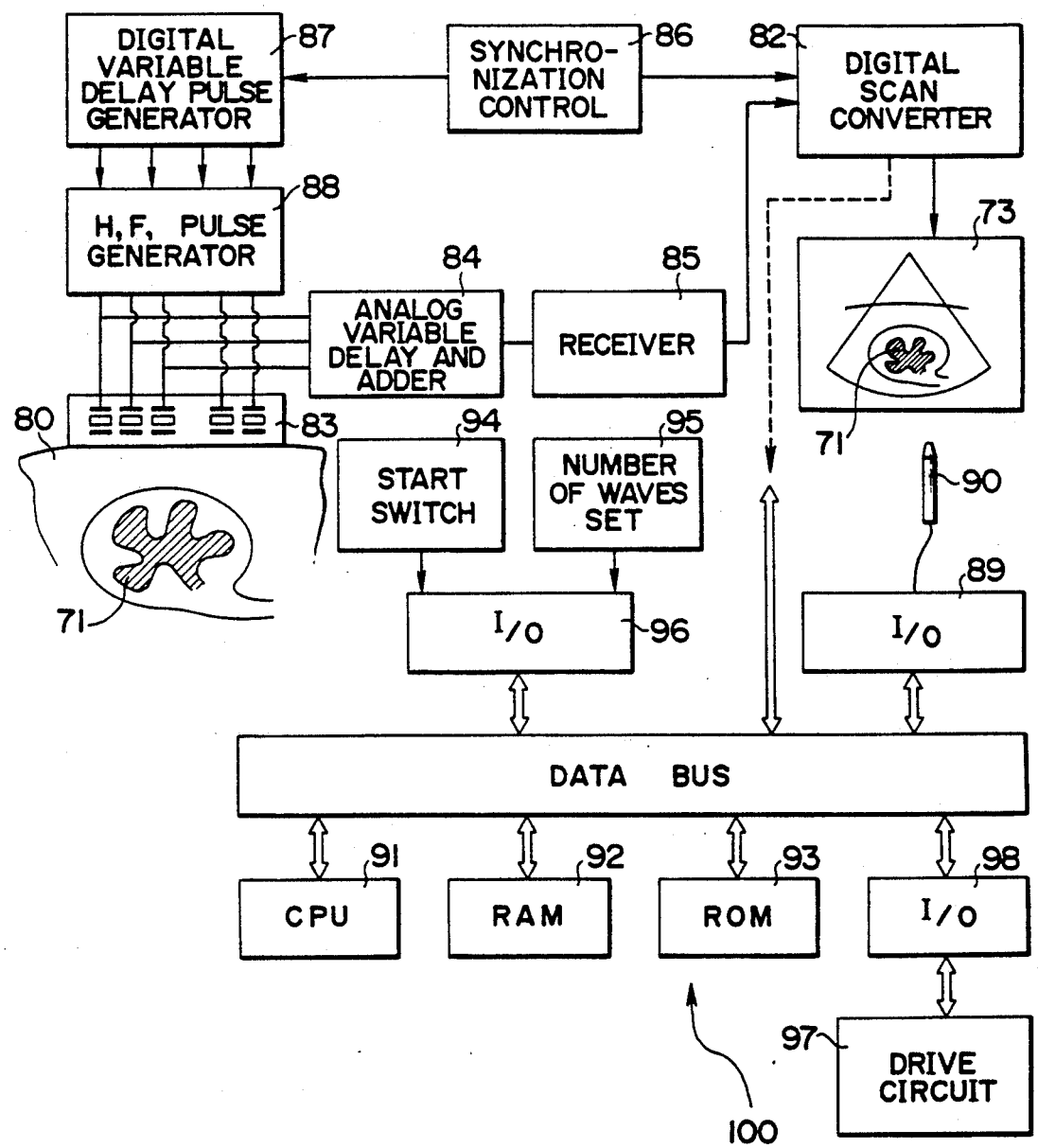
FIG. 14 is a block diagram of an ultrasonic therapeutical apparatus according to a sixth embodiment of the invention.

FIG. 14 shows a ultrasonic therapeutical apparatus according to a sixth embodiment of the invention which is designed to emit the ultrasonic wave for a calculus existing in a designated region and which is susceptible to motion as by a breathing operation, at the instant when the target calculus is most probably located in the region.

Specifically, a monitor display 73 is fed with a calculus location signal from a digital scan converter 82 for displaying an image of the calculus. A calculus 71 within a patient 80 is detected by an ultrasonic detector 83, which feeds a signal to the converter 82 through an analog variable delay and adder 84 and a receiver 85. A digital variable delay pulse generator 87 is then synchronized with the converter 82 through a synchronization control circuit 86, and controls a high frequency pulse generator 88, which feeds the ultrasonic detector 83. The detector 83 comprises a planar array of elements, and hence the delay pulse generator 87 is used to delay pulses for the purpose of focussing.

A positioning signal as from a light pen 90 is fed through I/O port 89 to be stored in a control memory 100 which comprises CPU 91, RAM 92 and ROM 93 so as to be delivered to the display 73 at suitable times. A shock wave start switch 94 and a number of shock waves presetting circuit 95 are connected to the memory through I/O port 96, and a shock wave generator drive circuit 97 is connected to a data bus through an I/O port 98.

Figure 15:
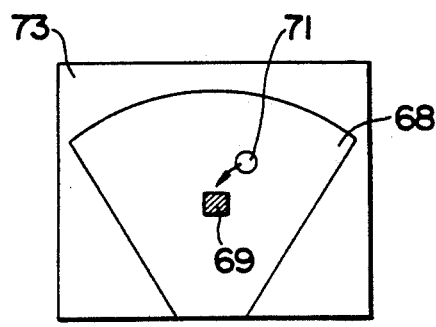
FIG. 15 is an illustration of a monitor screen of a display unit shown in FIG. 14.
Figure 16:
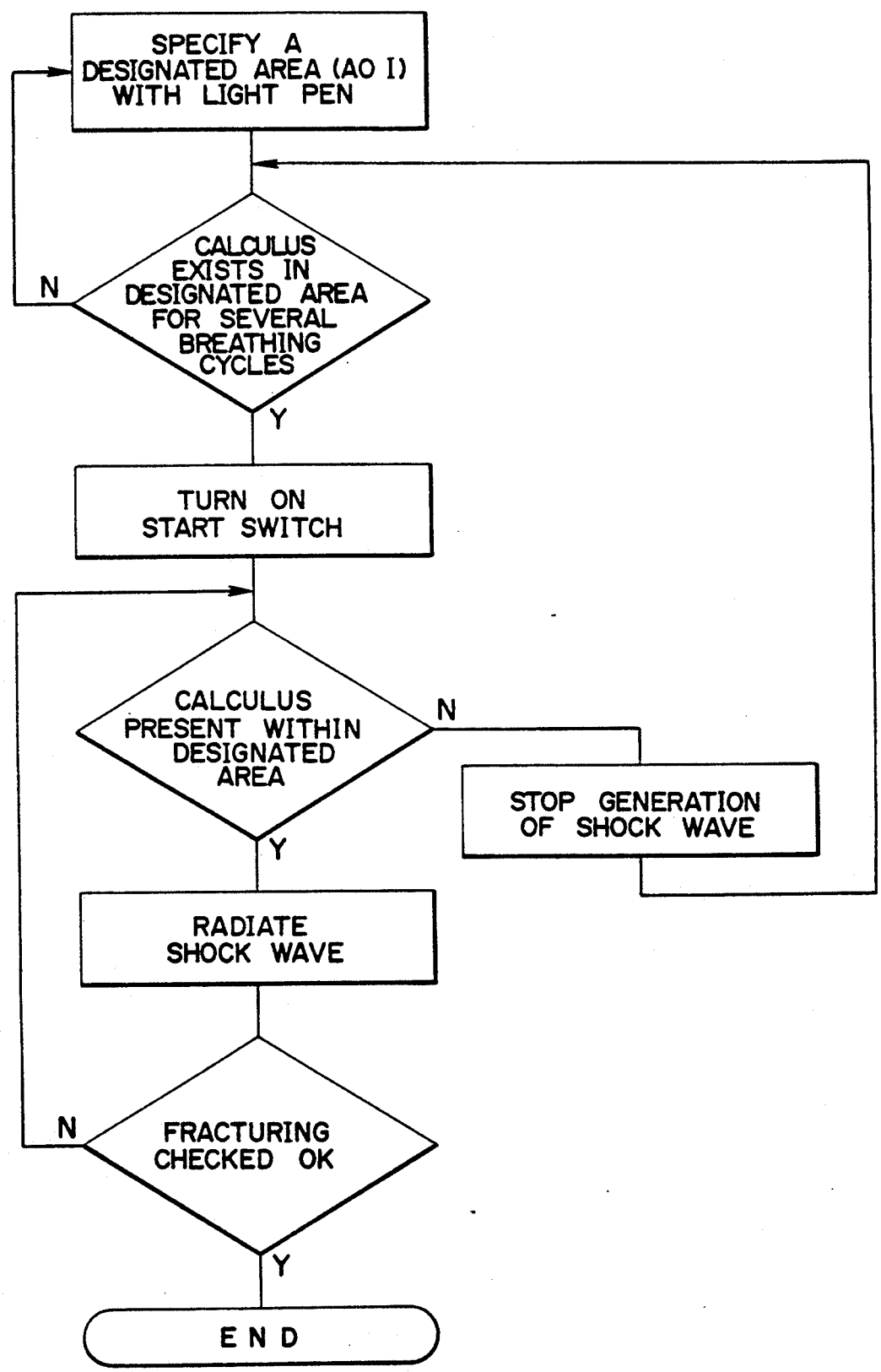
FIG. 16 is a flowchart illustrating the operation of an ultrasonic therapeutical apparatus according to the invention.

The operation of the therapeutical apparatus shown in FIG. 14 will be described below with reference to FIGS. 15 and 16. The location of the calculus 71 is detected by a measuring apparatus, not shown, and its image is displayed to allow a recognition of the number of calculi, its or their size, configuration and location. Such information is displayed on the monitor screen of the display 73 in a designated area. A region 68 subject to determination by an ultrasonic observation apparatus is indicated on the monitor screen of the display 73, as indicated in FIG. 15. Observing calculus information displayed on the monitor screen, an operator such as a physician specifies a designated area 69 (an area of interst-AOI) as by the light pen 90. Such area information is fed to and stored in the control memory 100 through the I/O port 89.

When the shock wave start switch 94 shown in FIG. 14 is turned on in order to fracture the calculus, the ultrasonic fracturing operation is initiated at the point in time when the designated area 69 stored in the control memory 100 coincides with the specified location of the calculus 71 which is determined by the ultrasonic measuring apparatus. Thus, CPU 91 triggers the shock wave generator drive circuit 97 a number of times preset in the circuit 98, through the data bus and I/O port 98. Each time the drive circuit 97 is triggered, the ultrasonic shock wave is emitted and directed to the calculus 71 at the specified location within the coeloma. If the location of the calculus 71 goes outside the specified area during the fracturing operation or when the location of the calculus 71 is out of the specified area from the beginning, CPU 91 does not deliver a trigger pulse if the start switch 94 is turned on. The calculus 71 which is to be treated can be recognized by a portion of ultrasonic data from the digital scan converter 82 which is above a threshold value and which is located within an area specified by the operator on the monitor screen of the display 33 as by the light pen 90. Accordingly, if the calculus moves as much as it goes out of the specified area due to a breathing operation, the ultrasonic shock wave generator is turned off, thus avoiding a wasteful emission of the ultrasonic shock wave.

Figure 17:
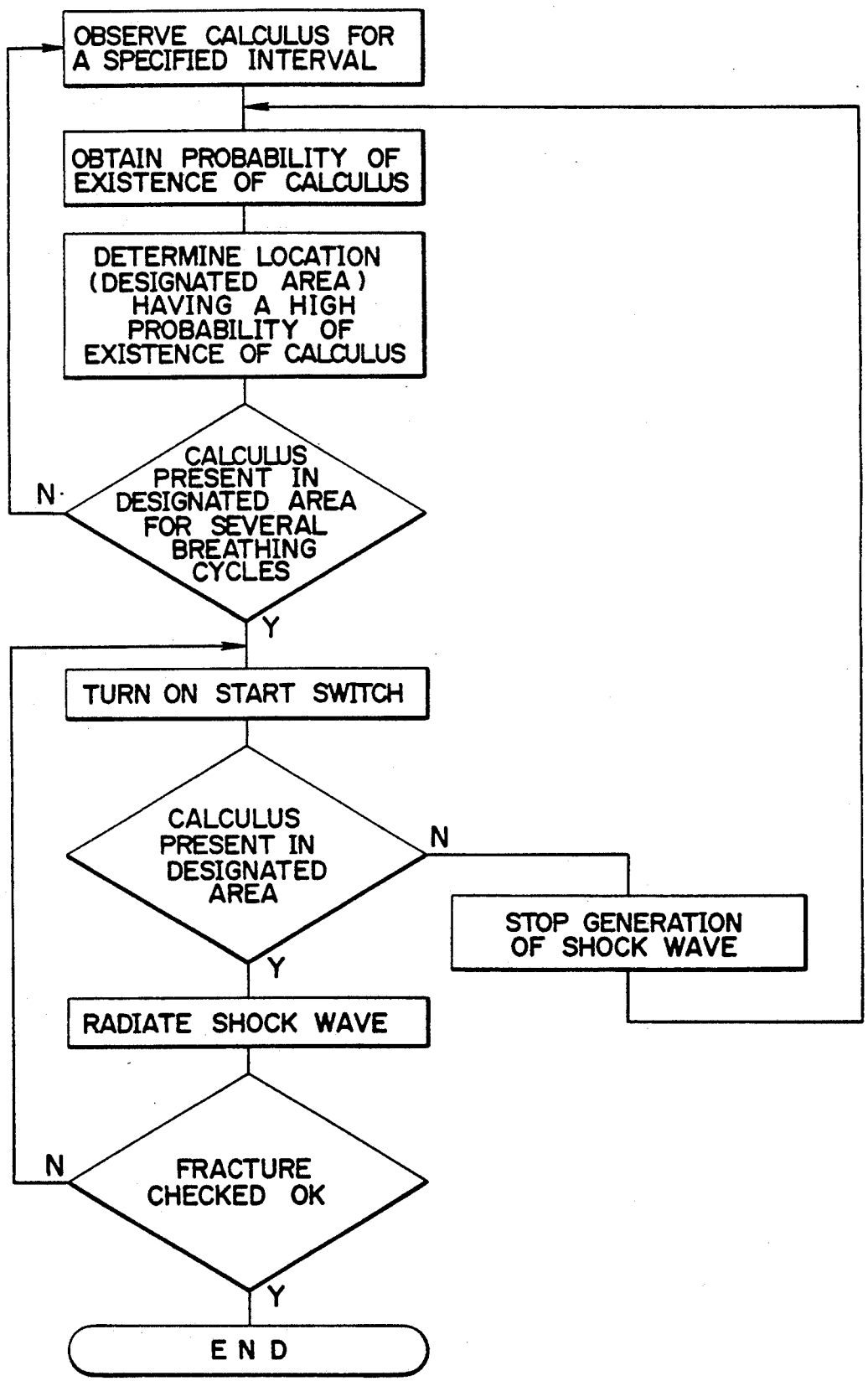
FIG. 17 is a flowchart of an operation of an ultrasonic therapeutical apparatus according to a seventh embodiment of the invention.

FIG. 17 is a flowchart for a seventh embodiment of the invention. Considering a renal calculus by way of example, a movement of the calculus 71 due to the breathing operation has a regular periodicity because the kidney moves in response to the breathing operation. Accordingly, when the calculus 71 is observed by the ultrasonic measuring apparatus for a given time interval, the location where the calculus 71 exists with a highest probability can be determined. Thus, by adding data stored in a frame memory (RAM 92) together over a given time interval, data representing a location where the calculus 71 exists for a longer time provides a greater sum, and is more intensely displayed on the display 73. In this manner, a distribution of the probability of the location where the calculus 71 exists is obtained. The location where the probability of the existence of the calculus 71 is high is then recognized, and the specified area 69 is specified on the monitor screen of the display 73 as by the light pen 90.

The ultrasonic shock wave is irradiated upon coincidence between the location of the calculus 71 which is determined by the image processing by the ultrasonic measuring apparatus and the specified area 69, but the shock wave generator cannot be turned on in the absence of such coincedence. In this manner, it is assured that the shock wave generator is turned on only when the calculus assumes a location where the probability of existence of the calculus 71 is at its maximum.

It is to be noted that the target to be treated according to the invention is not limited to the calculus 71 alone, nor the invention is limited to a calculus fracturing apparatus, but that the invention is equally applicable to any therapeutical apparatus in which the focussing of an ultrasonic wave upon a target is desired.

Figure 18:
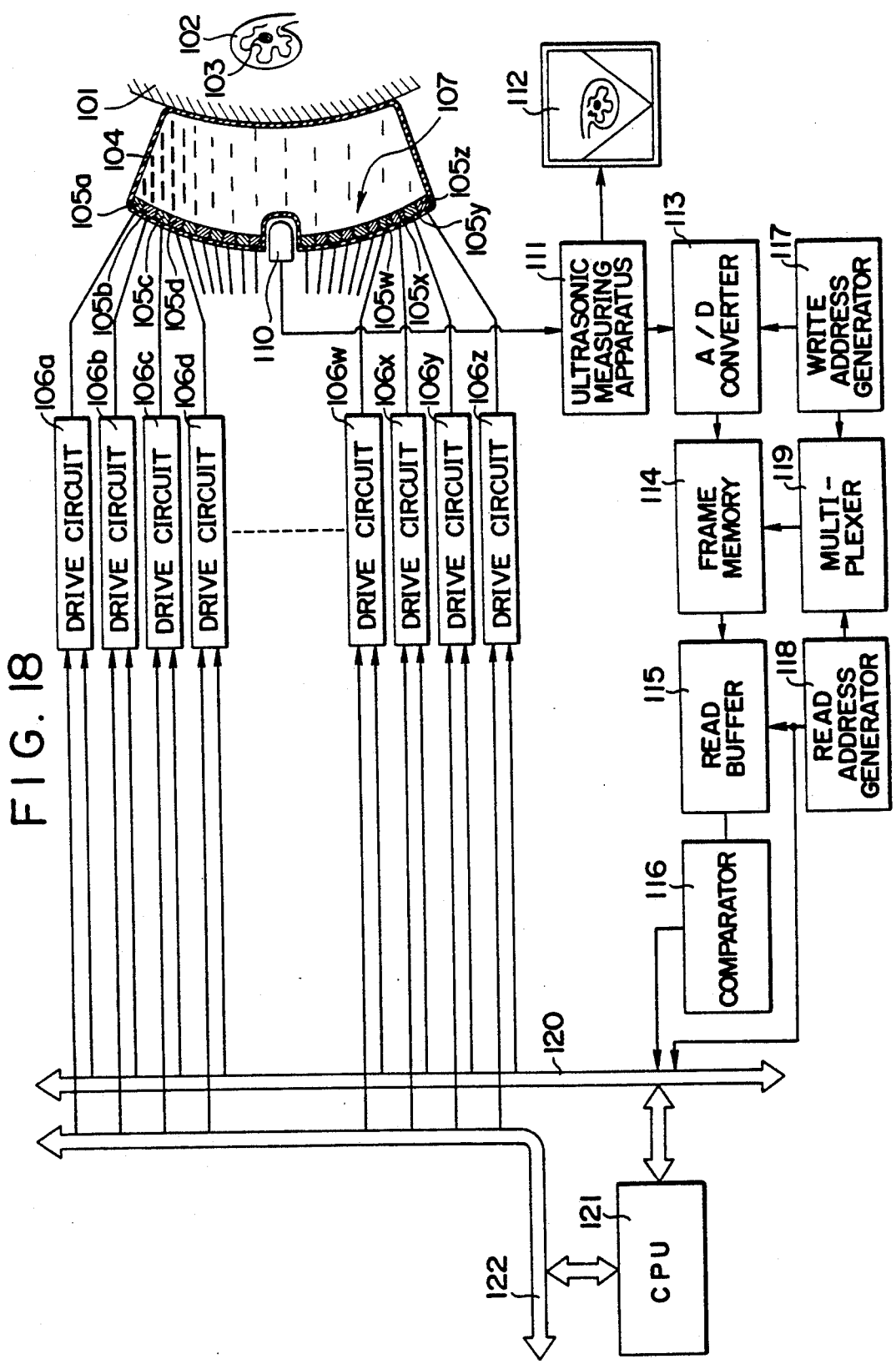
FIG. 18 is a block diagram of an ultrasonic therapeutical apparatus according to an eighth embodiment of the invention.

FIG. 18 shows an ultrasonic therapeutical apparatus according to an eighth embodiment of the invention which enables the focal position of the ultrasonic shock wave to be shifted simply and rapidly. It is assumed that a living body 101 includes kidney 102 in which a calculus 103, the target to be treated, is located. In order to fracture such calculus 103, a shock wave generator 107 comprising an array of ultrasonic vibrators 105a to 105z disposed along a spherical surface in a mosaic pattern is disposed in contact with the body 101 with a water filled bag 104 interposed therebetween. A number of vibrators 105a to 105Z greater than those shown in FIG. 18 may be employed.

Each of the ultrasonic vibrators 105a to 105z is connected to one of drive circuits 106a to 106z, each of which applies a drive voltage to its associated vibrator to cause the latter to generate an ultrasonic shock wave. An ultrasonic probe 110 of mechanical scan type is disposed at the center of the array of the vibrators 105a to 105z. The probe 110 is connected to an ultrasonic measuring apparatus 111, which feeds its output to CRT monitor 112, and an analog/digital (hereafter abbreviated as A/D) converter 113. An output from the converter 113 is written into a frame memory 114. The frame memory 114 includes a memory area which corresponds to the screen of the monitor 112. Data read out of the memory 114 is fed through read-out buffer circuit 115 to a comparator 116. A multiplexer 119 which switches between outputs of a write address generator 117 and a read address generator 118 is connected to the memory 114. An output from the comparator 116 and an output from the read address generator 118 are fed through a data bus 120 to CPU 121.

An address bus 122 is connected to CPU 121, and both the address bus 122 and the data bus 120 are connected with the drive circuits 106a to 106z. Peripheral circuits associated with CPU 121 such as memories and clock circuits are omitted from illustration as is a power supply for the drive circuits 106a to 106z.

In operation, the ultrasonic probe 110 performs a sector scan with its ultrasonic wave output to derive an echo signal from the living body 101, kidney 102m and calculus 103 under the condition that the shock wave generator 107 is disposed in contact with the body 101 with the bag 104 interposed therebetween. The echo signal is processed in the ultrasonic measuring apparatus 111 to derive a signal which represents a tomographic image of an object being examined, whereby the tomographic image is displayed on CRT monitor 112. The tomographic image signal which is output from the apparatus 111 is fed to the converter 113, and each picture element signal is written into the frame memory 114. At this time, the multiplexer 119 selects an output from the write address generator 117, thus supplying a series of write addresses to the memory 114.

When data representing one frame of tomographic image has been written into the memory 114, the multiplexer 119 switches to select an output from the read address generator 118, thus reading data from the memory and supplying it to the comparator 116 through the buffer 115. The comparator 116 is effective to determine that a particular picture element in the frame represents the surface of the body 101 when its corresponding signal exceeds a threshold value. In response to addresses of those picture elements which represent the surface of the body 101 and supplied to CPU 121 through the data bus 120, CPU 121 operates to determine the distance from the surface of the body 101 to the location of the calculus 103 within the kidney 102. It then calculates the distance from the shock wave generator 107 to the focal point of the ultrasonic shock wave. CPU 121 then activates selected ultrasonic vibrators for emission of an ultrasonic shock wave, depending on the distance calculated. For example, for a near distance, the vibrators 105a to 105q are selected, and for a medium distance, the vibrators 105f to 105u are selected. The selection of particular ultrasonic vibrators which are driven is equivalent to choosing an aperture radius of the shock wave generator 107. A change in the aperture radius of the shock wave generator 107 results in a variation in the focal position of the ultrasonic shock wave, thus allowing the focal position of the ultrasonic shock wave to be coincident with the location of the calculus 103. This aspect will be dealt with in more detail.

It is well recognized that the acoustical field of a circular concave-surface vibrator is very complex. However, Rayleigh's formula provides a sound pressure on a central axis divided by a mean sound pressure on a radiating surface as follows:

$$P_A = \left| \frac{P_A}{P_0} \right| = \left| \frac{2R}{R-Z} \sin\left( \frac{\pi}{2} \cdot \frac{a^2}{\lambda R^2} \cdot \frac{R-Z}{2} \right) \right|$$

Where R represents the radius of curvature, $\lambda$ the wavelength in a medium, a the radius of a vibrator and a the distance. While the formula appears to be complicated in nature, it may assumed that R, $\lambda$ and $P_A$ are constants, thus reducing the formula to a relationship between a and z. Thus, assuming that the radius of curvature, the drive frequency and the sound pressure are constant, the distance z to the focal position of the ultrasonic shock wave may be changed by changing the radius of the vibrator. By way of example, when a drive frequency of 300 kHz and a radius of curvature of 100 mm are used, changing the radius of the vibrator in a range from 13 to 28 mm results in changing the distance to the focal position from about 20 mm to 115 mm. Thus, a number of ultrasonic vibrators which are to be driven may be chose depending on the distance. If the calculus 103 is located nearer the shock wave generator 107, a smaller aperture radius may be chose for the shock wave generator 107. Conversely, when the calculus 103 is located further from the generator 107, a larger aperture radius may be chosen. In this manner, the focal position of the ultrasonic shock wave may be brought into coincidence with the location of calculus 103. When a reduced aperture radius is used, the number of vibrators which are driven decrease, thus decreasing the power which is available at the focal position of the shock wave. However, the voltage applied to each vibrator which is driven may be increased, thus feeding a greater power to each vibrator to achieve the power of the same level at the focal position, thus maintaining a fracturing power of the same level. In this manner, the eighth embodiment permits the focal position of shock wave to be freely changed in the radial direction or in the direction of depth by merely increasing or decreasing the number of vibrators driven to change the aperture radius, without accompanying a movement of the shock wave generator 107.

If the calculus 103 moves in response to a breathing operation, the ultrasonic measuring apparatus 111 is able to index such location as mentioned previously, and hence CPU 121 can choose a particular group of ultrasonic vibrators which are to be driven, thus maintaining the focal position of the shock wave coincident with the location of the calculus. It is to be noted that this embodiment is also applicable to any arrangement in which it is necessary to focus an ultrasonic wave upon a target to be treated, rather than being limited to a calculus fracturing apparatus.

Figure 19:
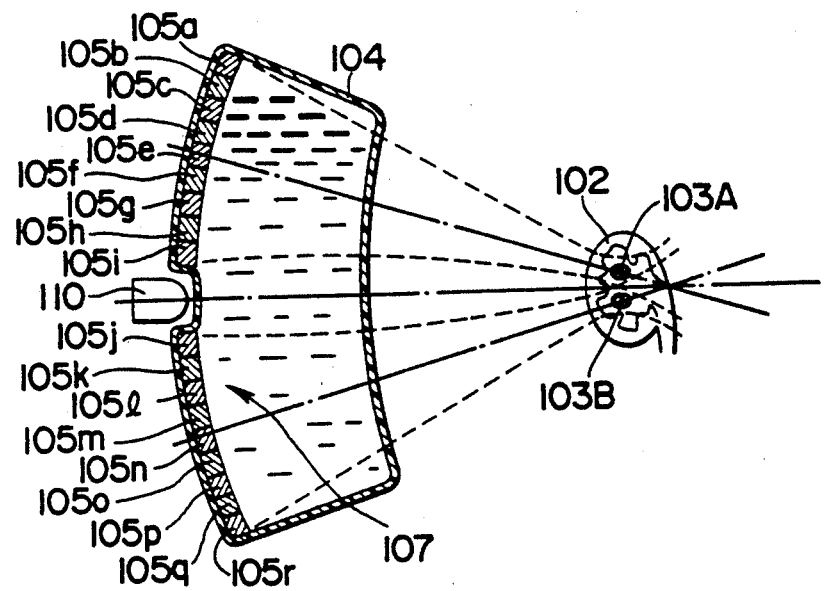
FIG. 19 is a fragmentary cross section of an ultrasonic therapeutical apparatus according to a ninth embodiment of the invention.

FIG. 19 shows an essential part of a ninth embodiment of the invention. When a particular group of ultrasonic vibrators, 105a to 105i, for example, is chosen which are centered about an ultrasonic vibrator 105e, the focal position of the ultrasonic shock wave may be located at an upper focal position 103A shown in FIG. 19. Alternatively, when a group of ultrasonic vibrators 105j to 105r which are centered about an ultrasonic vibrator 105n is chosen, the focal position of the shock wave shifts to a lower focal position 103B shown in FIG. 19. In this manner, an equal number of ultrasonic vibrators located on either side of a particular ultrasonic vibrator may be freely driven to shift the focal position of the ultrasonic shock wave in the same direction as the shock wave generator 107. The general arrangement including ultrasonic measuring apparatus and the data bus remains the same as in the same as in the eighth embodiment, and hence is omitted from illustration.

Figure 20:
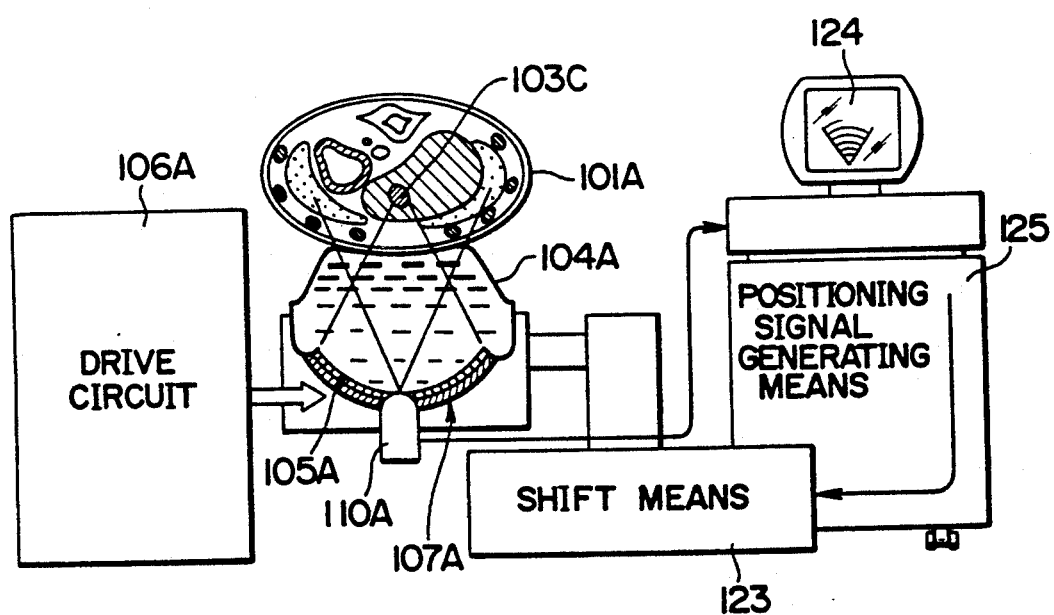
FIG. 20 is a schematic illustration of an ultrasonic therapeutical apparatus according to a tenth embodiment of the invention.

FIG. 20 shows a tenth embodiment of the invention. Specifically, a shock wave generator 107A including a water bag 104A which is filled with water is connected to a drive circuit 106A and is carried by shift means 123. The location of a calculus 103C within a living body 101A is recognized by the combination of an ultrasonic probe 110A and ultrasonic measuring apparatus 124, and the shock wave generator 107A is moved through an increased stroke by means of positioning signal generator 125 and the shift means 123 in order to bring the focus of the generator 107A into coincidence with the location of the calculus 103C. When the focus of the generator 107A is brought into coincidence with the calculus 103C, this remains to be a temporary condition, and the calculus 103C continues to change its position due to a breathing operation. This makes it difficult to maintain the focus of the generator 107A in coincidence with the location of the calculus 103C. Accordingly, ultrasonic vibrators 105A which are contained in the generator 107A selectively driven in the same manner as described above in connection with the eighth and the ninth embodiment to shift the focal position of the ultrasonic shock wave, thereby bringing the focal position into alignment with the calculus 103C. In this manner, the focal position of the ultrasonic shock wave is moved through an increased stroke by the shift means 123 which carries the generator 107A, and is rapidly moved through a reduced stroke by a selective energization of particular ultrasonic vibration which are driven.

Figure 21:
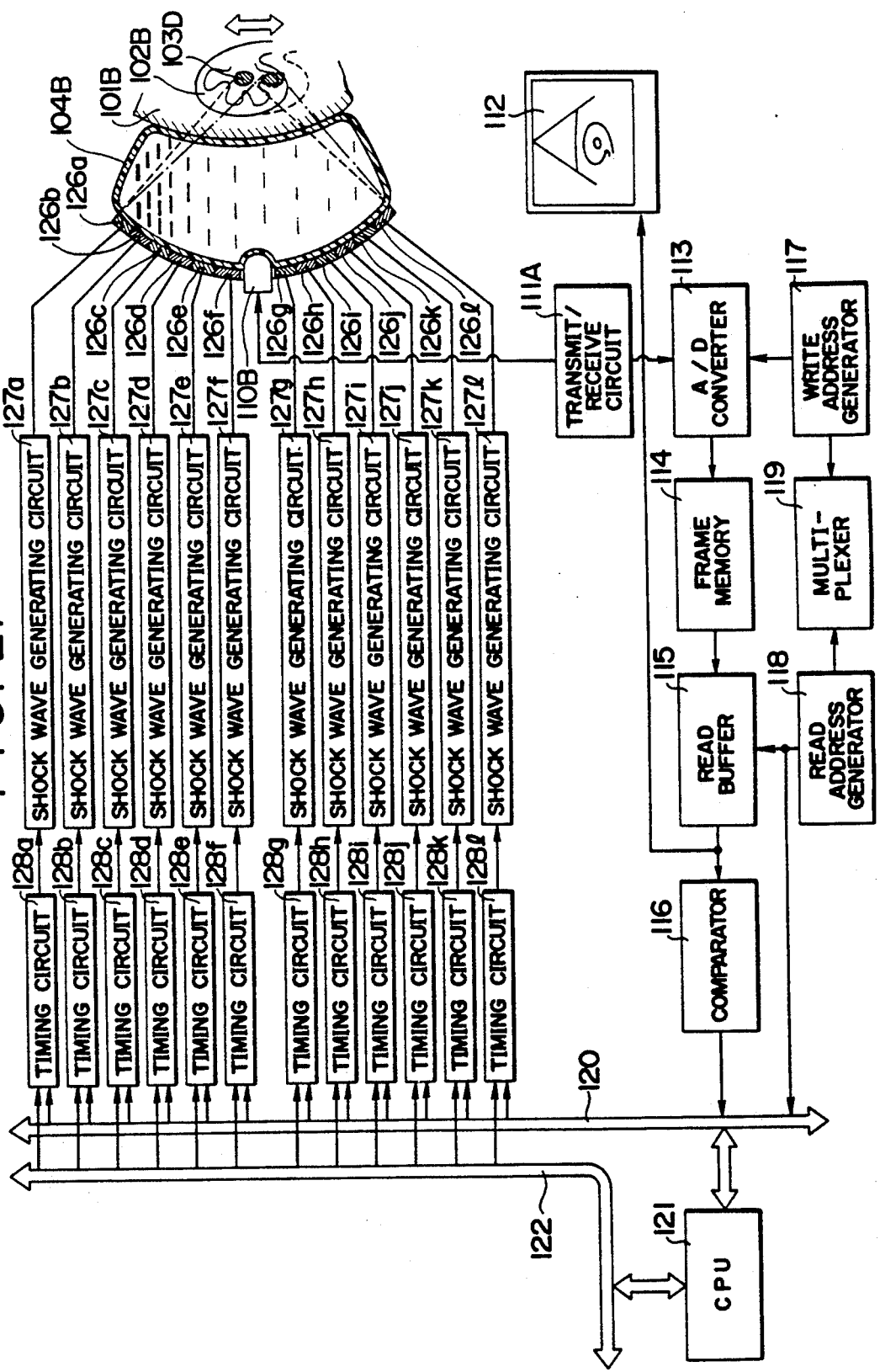
FIG. 21 is a block diagram of an ultrasonic therapeutical apparatus according to an eleventh embodiment of the invention.

FIG. 21 shows a ultrasonic therapeutical apparatus according to an eleventh embodiment of the invention which is designed to concentrate the ultrasonic wave upon an effected area by controlling the timing of focussing of the ultrasonic waves developed by the ultrasonic vibrators. Specifically, a living body 101B includes a kidney 102B in which a calculus 103D to be treated is situated. In order to fracture the calculus, a probe comprising piezoelectric elements 126a to 126l disposed along a quadratic surface in a mosaic pattern is brought into contact with the living body 101B with a water bag 104B which is filled with water interposed therebetween. It is to be understood that a number of piezoelectric elements greater those shown are used in actuality, but the illustration is simplified for the purpose of convenience. Piezoelectric elements 126a to 126l are connected to shock wave generating circuits 127a to 127l, respectively, which apply a pulse voltage to the associated elements 126a to 126l to cause the latter to produce a shock wave of an increased intensity which is sufficient to destroy the calculus. The generating circuits 127a to 127l are connected to timing circuits 128a to 128l, respectively, which control the timing of generating the shock wave.

The piezoelectric elements 126a to 126l are disposed along an arc, and an ultrasonic probe 110B of mechanical scan type is disposed between the central ones of the piezoelectric elements, namely, 126f, 126g, for the purpose of observation. The probe 110B is connected to a transmit/receive circuit 111A. When a transmission signal is delivered from the circuit 111A to the probe 110B, the latter produces an ultrasonic beam which is directed toward a coeloma, and the beam which is reflected by the calculus 103D located within an affected part is received by the probe 110B and then fed to the receive circuit 111A, thus allowing the location of the calculus 103D to be detected. The reception output from the circuit 111A is supplied to an A/D converter 113.

Selected signals which are processed by the circuit 111A are fed to CPU 121, and the memory cycle takes place in substantially the same manner as described above in connection with the eighth embodiment shown in FIG. 18, and therefore will not specifically described, except to note that corresponding parts are designated by like reference numerals. It is to be noted that address bus 122 and a data bus 120 are connected to the timing circuit 128a to 128l.

In operation, the probe comprising the piezoelectric elements 126a to 126l is brought into contact with the living body 101B through the interposed water bag 104B. The probe 110B performs a sector scan, thus deriving an echo signal from the living body 101B, the kidney 102B and the calculus 103D. The echo signal is processed by the transmit/receive circuit 111A, and fed through a frame memory 114 to derive a signal respecting a tomographic image of an object being examined. The tomographic image is displayed on CRT display 112. While observing the display 112, an operator adjusts the location of the water bag and the probe, so that the focal position of the quadratic surface along which the piezoelectric elements 126a to 126l are disposed coinides with the location of calculus 103D. Such adjustment takes place by known means which is disclosed in U.S. Pat. No. 4,617,931.

Data read from the frame memory 114 is fed through a red buffer circuit 115 to a comparator 116, which is operative to extract the address of only those signals having levels greater than a given value, and these addresses are fed to the data bus 120 together with data from the read address generator 118. In this manner, CPU 121 stores the addresses of only those signals having a high brightness. The extracted addresses represent a digital value indicative of the location of the calculus. The timing with which the piezoelectric elements 126a to 126e are driven are adjusted to focus the ultrasonic beam which is produced by these elements upon the location of the focus thus determined.

Figure 22:
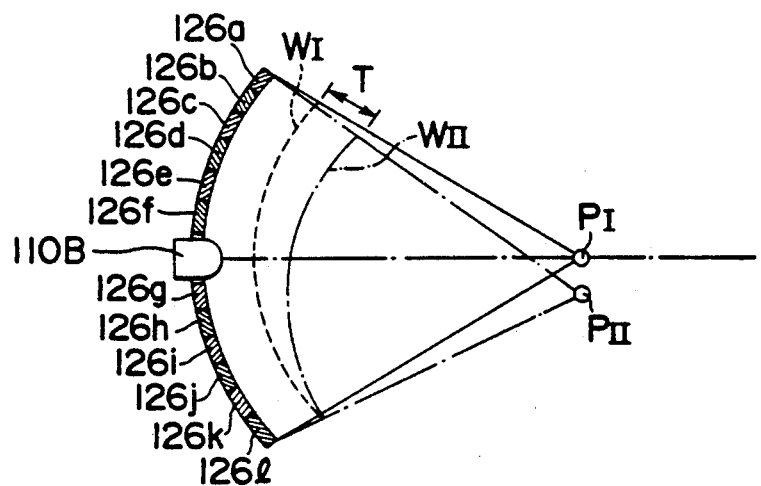
FIG. 22 is a diagram illustrating the relationship between the wave surface and the focal position in the arrangement shown in FIG. 21.

FIG. 22 is an illustration of bringing and maintaining the focal position of an ultrasonic beam emitted by the piezoelectric elements 126a to 126l into and in coincidence with the location $P_I$ or $P_{II}$ of the calculus 103D. An ultrasonic wave transmitting surface comprising a two-dimensional spherical shell is developed in front of the piezoelectric elements 126a to 126l, as indicated in dotted lines in FIG. 22. Assuming that the focal position of the ultrasonic wave having the wave surface $W_I$ coincides with the location $P_I$ of the calculus, if the calculus 103D moves from the location $P_I$ to $P_{II}$ as a result of a breathing operation, for example, the focal position must be rapidly moved from $P_I$ to $P_{II}$ in following relationship therewith, thus displacing the transmitting wave surface $W_I$ to another transmitting wave surface $W_{II}$. In order to achieve the wave surface $W_{II}$, the timing of a signal applied to the piezoelectric element 126a is chosen to be by a time interval T earlier than the timing of a signal applied to the piezoelectric element 126l. The same is true with respect to the remaining elements 126b to 126k.

Figure 23:
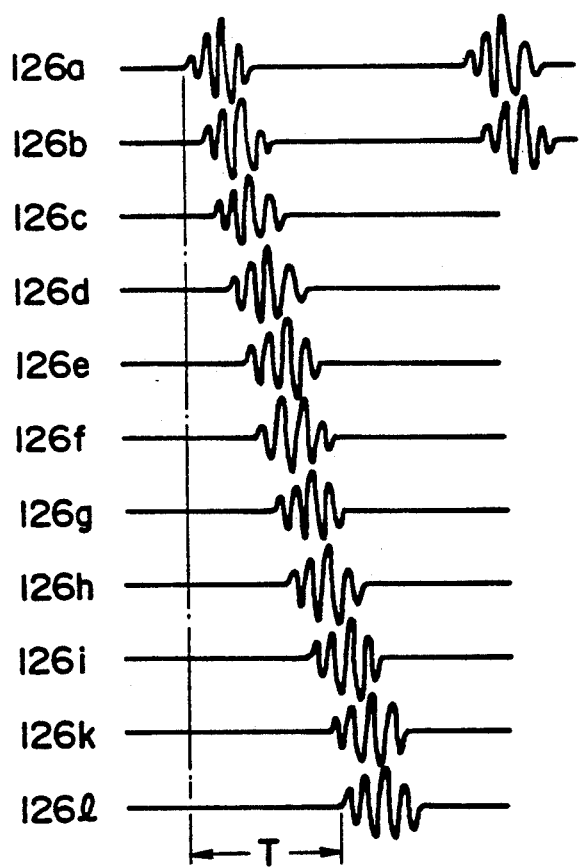
FIG. 23 graphically shows the waveforms of ultrasonic signals from individual piezoelectric elements used in the arrangement of FIG. 21.

Signals which are used to drive the piezoelectric elements 126a to 126l are derived by the shock wave generating circuits 127a to 127l, in a manner illustrated in FIG. 23. The relative timing between the signals applied to the individual piezoelectric elements is determined by the timing circuits 128a to 128l by signals which are delivered thereto from CPU 121 over the data bus 120. In this manner, a time difference T between the wave surfaces WI and WII is achieved.

Figure 24:
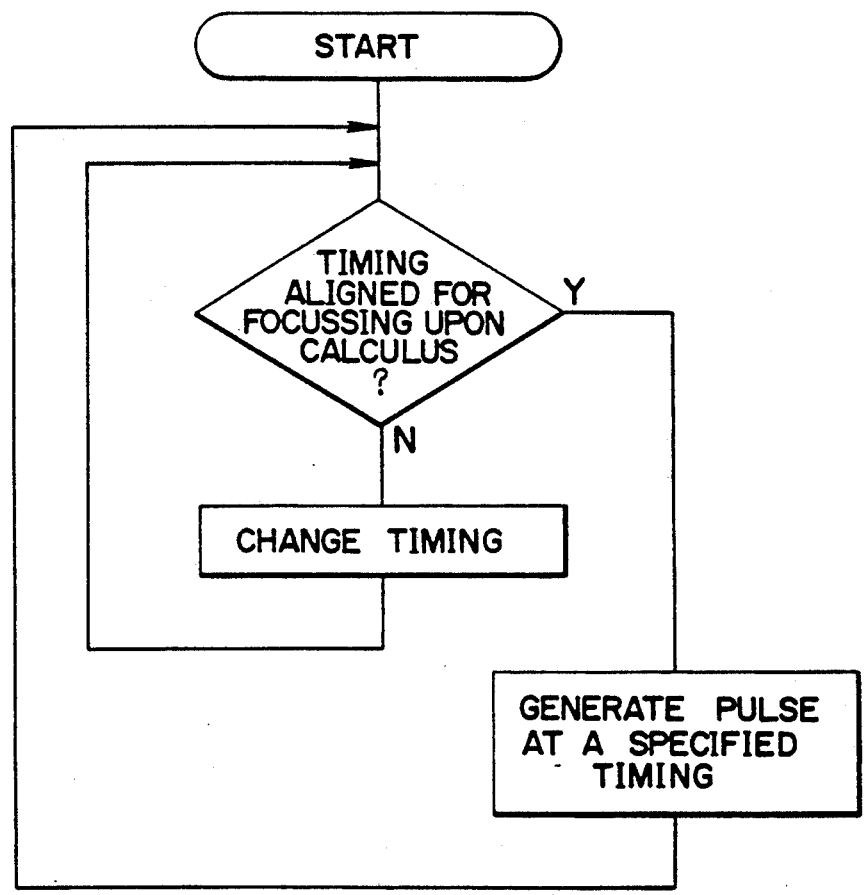
FIG. 24 is a flowchart of the operation of the arrangement shown in FIG. 21.

FIG. 24 is a flowchart of a timing control. Specifically, the location of a calculus is compared against a focal position which is expected from the prevailing timing. If a coincidence therebetween is not reached, the timing is modified, while the present timing is used to develop pulses if the coincidence is maintained. In this manner, the timing of driving the individual piezoelectric elements which are distributed in three dimensions along a spherical surface in a mosaic patter is controlled to achieve a focal position which automatically tracks the location of the calculus.

In this manner, in accordance with this embodiment, data representing a location of an affected area is derived by means which continuously operates to detect the location of such area. Such data is utilized to drive focussing means to bring the focal position into coincidence with the location of the affected area, the focussing means comprising a control over the timing with which the individual piezoelectric elements are drive. In this manner, a focussing is accomplished without any time lag in the presence of a movement of the effected area, thus improving the efficiency of fracturing a calculus as well as the safety due to the elimination of any damaging of normal tissues.

Figure 25:
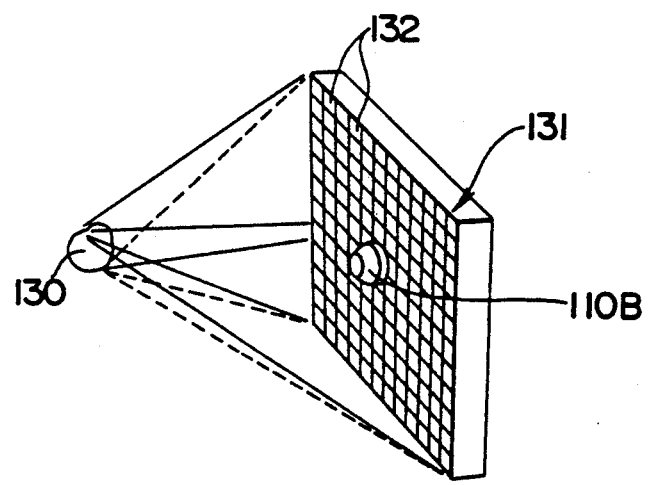
FIG. 25 is a perspective view of an ultrasonic therapeutical apparatus according to a twelfth embodiment of the invention.

FIG. 25 is an illustration of part of a twelfth embodiment of the invention which is applied to a thermal therapy of tumor. In this embodiment, the arrangement is generally similar to the eleventh embodiment except that a number of piezoelectric elements 132 are disposed in a matrix forming a plane, thus constituting together a group 131 thereof. An ultrasonic probe 110B is disposed at the center of the matrix to detect the location of a tumor 130, and the groups of piezoelectric elements 131 emits an ultrasonic beam which is directed toward the tumor 130 for a thermal therapy thereof. Where the tumor 130 has an extensive area, a scan of the ultrasonic beam may be utilized.

Figure 26A:
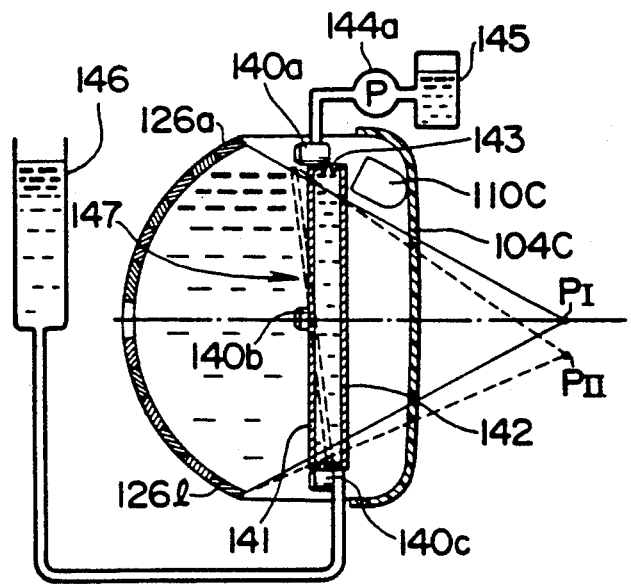
FIGS. 26A, B and C illustrate an ultrasonic therapeutical apparatus according to a thirteenth embodiment of the invention.
Figure 26B:
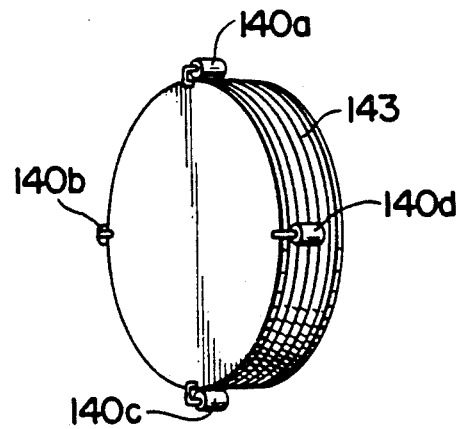
FIG. 26B being a perspective view of an acoustical prism.
Figure 26C:
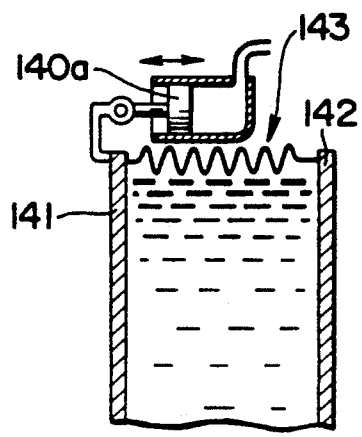
FIG. 26C being a fragmentary cross section, to an enlarged scale, of a piston in relation to the acoustical prism.

FIGS. 26A to 26C show a thirteenth embodiment of the invention which utilizes an acoustical prism in order to change the focal position of the ultrasonic shock wave rapidly. Referring to FIG. 26A, and acoustical prism 147 comprising a pair of oppositely located lid plates, 141, 142 of an equal size and configuration and connected together by bellows 143 is contained within a water bag 104C. The internal space defined between the lid plates is filled with a liquid having an acoustical refraction index greater than that of a liquid contained within the water bag 104C and which is supplied from a liquid tank 146. As illustrated in FIGS. 26A to 26C, four pistons 140a to 140d are disposed at an equal interval around the acoustical prism 147 to permit the spacing between the lid plates to be changed at will. Specifically, each of the pistons 140a to 140d includes a cylinder chamber which is connected through an associated pump 144a to 144d (144b to 144d being not shown) to an oil tank 125, as illustrated in FIG. 26A. The pumps 144a to 144D are controlled by a processor, not shown. An ultrasonic probe 110C which are used to detect the location of a calculus is disposed intermediate the acoustic prism 147 and the calculus.

In operation, a movement of the calculus from location $P_I$ to a location $P_{II}$ is detected by the ultrasonic probe 110C, and an address signal corresponding to the location $P_{II}$ is fed to the processor mentioned above, which then responds thereto by calculating the orientation in which the ultrasonic beam is to be focussed, delivering the control signals fed to the pumps 144a to 144d. By activating the pistons 140a to 140d in a corresponding manner, the configuration of the acoustic prism 147 may be modified so that the ultrasonic beam is focussed upon the location $P_{II}$ of the calculus. Thus, referring to FIG. 26A, when the lid plate 141 of the acoustical prism 147 is located as indicated by the solid line, the ultrasonic wave emitted by the piezoelectric elements 126a to 126l is focussed upon the location PI, but as the piston 140a projects while the piston 140c retracts into its cylinder to displace the lid plate 141 of the acoustical prism 147 to the dotted line position to thereby change the acoustic impedance, the focussing direction shifts downward, as viewed in this Figure, whereby the ultrasonic wave can be focussed on the location $P_{II}$. In this manner, the focal position of the ultrasonic wave may be changed rapidly, enabling a quick, automatic tracking operation. A change in the volume of the acoustical prism 147 takes place by increasing or decreasing the liquid quantity in the liquid tank 146.

FIG. 27 is a schematic illustration of an ultrasonic therapeutical apparatus according to a fourteenth embodiment of the invention, which is designed to cover an extended area to facilitate determining the location of a calculus before it is treated. There is shown the physical body 151 of a patient which contains a calculus 152 therein. A pair of ultrasonic probes of electronic scan type 153, 154 are used to obtain a tomographic image over an area encompassed by a pair of dotted lines 165, 166. The probed 153 is disposed for angular movement as by a probe driver 158 which may comprise a stepping motor, for example. On the other hand, the probe 154 is disposed for angular movement as well as for movement in three dimensions by a probe driver 158 which may comprise a stepping motor or X-Y-Z stage. The probe 153 is disposed at the center of an ultrasonic wave generator 155 while the probe 154 is located at a lateral position adjacent thereto. The generator 155 comprises a number of ultrasonic vibrators disposed in an array along a spherical shell to produce an ultrasonic wave of an increased intensity at the focus F of the shell in response to a drive from a drive circuit 156. A water bag (not shown) comprising a soft resin material and filled with an ultrasonic wave transmitting medium such as water is interposed between the generator 155 and the patient 151.

An ultrasonic measuring apparatus 159 delivers a transmit pulse to the probes 153 and 154 through a rotary transformer 157, and a received pulse from the probes 153, 154 are fed through the transformer 157 back to the observation apparatus 159 so as to be displayed as a B-mode image. The rotary transformer 157 is of a conventional form, and is constructed to permit an electrical signal to be transmitted to a rotating member without using any electrical contact. Image information from the measuring apparatus 159 is fed to an image processor 160 where the coordinates of the center of gravity of the calculus is calculated. A location detector 161 responds to a difference between the coordinates of the center of the gravity and the coordinates of the focus F of the generator 155, by causing a position controller 162 to drive a shifting unit 163 so as to bring the both points into coincidence until the difference is removed.

In operation, when a tomographic image acquired by the probe 153 fails to locate a calculus, the probe 154 is initially rotated about its center axis 168 while causing it to revolve about the center axis 169 of the generator 155, thus causing it to scan across an extensive area in X, Y and Z directions, thus searching for the calculus 152 within the patient 151. If the presence of a calculus is recognized in a certain tomographic image, such position information is utilized to cause the position controller 162 to drive the shifting unit 163 so as to move the location of the calculus 152 into a measurable range 165 having the focus F of the generator 155 on its center axis 169. After such movement, the location of the calculus 152 is automatically tracked on the basis of a tomographic image from the probe 153, covering the measurable range 165 for performing a fracturing operation.

Specifically, an ultrasonic echo signal from the probe 153 is fed through the rotary transformer 157 to the measuring apparatus 159 where a B-mode image is obtained. This information is then fed to the image processor 160 where digitization and a calculation of an area are made to extract the calculus 152, the position of the center of gravity of which is then calculated and delivered to the location detector 161. The location detector 161 detects a difference between the location of the center of gravity and the location of the focus F, and the difference signal is output to the position controller 162. The position controller 162 is effective to drive the shifting unit 163 so that the both points are brought into coincidence with each other. The described operation is repeated to perform a focussing operation continuously. Thus, in this embodiment, the use of the searching probe 154 significantly extends the measurable range, facilitating the coarse location of the calculus to be determined. The automatic tracking of the calculus drastically improves the efficiency of the fracturing operation.

In this embodiment, it is assumed that the center of gravity of a calculus, as determined by the processing of echo signals, represents the actual location of the calculus during the automatic tracking of the calculus. However, a fracturing operation may also be contemplated in which the size of a calculus is determined on the basis of the area of echo-throughs 150A, 150B (see FIG. 21), and the fracturing operation is continued until this area reduces below a given value. It is also possible to detect the size of the calculus by a treatment which removes the respective echo-throughs.

Figure 28:
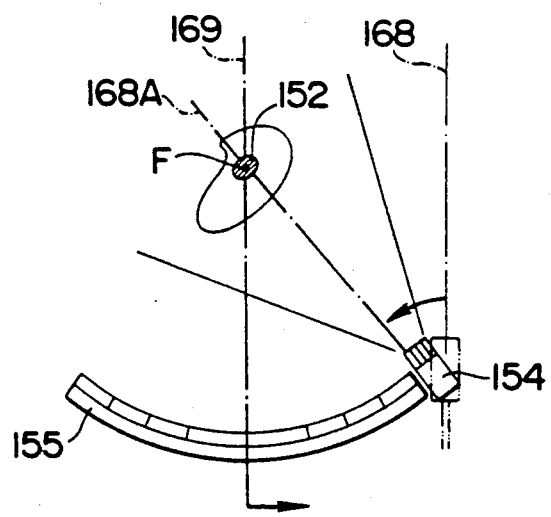
FIG. 28 is a schematic illustration of an ultrasonic therapeutical apparatus according to a fifteenth embodiment of the invention.
Figure 29:
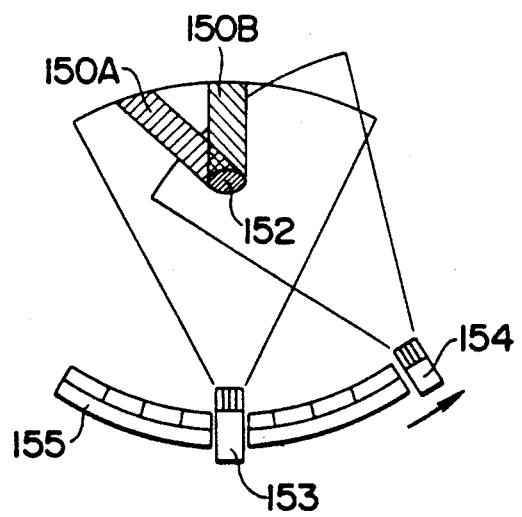
FIG. 29 is a diagram illustrating an echo-through which may occur in a tomographic image formed by an ultrasonic probe.

FIG. 28 is a schematic illustration of an ultrasonic therapeutical apparatus according to a fifteenth embodiment of the invention, which is generally similar to the apparatus shown in FIG. 27 except that a searching probe 154 has an oscillatable axis 168 which is directed toward the center axis 169 on which the focus F of the ultrasonic wave generator 155 is located. The oscillation of the probe 154 enables it to oscillate in a direction indicated by an arrow in following relationship with the calculus 152 during the time the generator 155 is moved so as to bring the focus F thereof into coincidence with the calculus after the calculus 152 has been found on the axis 168A, thus maintaining its axis 168A in alignment with the location of the calculus. After the generator has been focussed upon the calculus 152, the location of the calculus 152 is automatically tracked on the basis of a tomographic image acquired by the probe 154 for purpose of a fracturing operation. With this embodiment, an advantage that a simplified construction of a smaller size may be employed by dispensing with the centrally located probe 153, in addition to the effects of the apparatus of the fourteenth embodiment. FIG. 29 illustrates echo-throughs 150A, 150B caused by the presence of the calculus 152 in a tomographic image acquired by the probes 153, 154.

Figure 30:
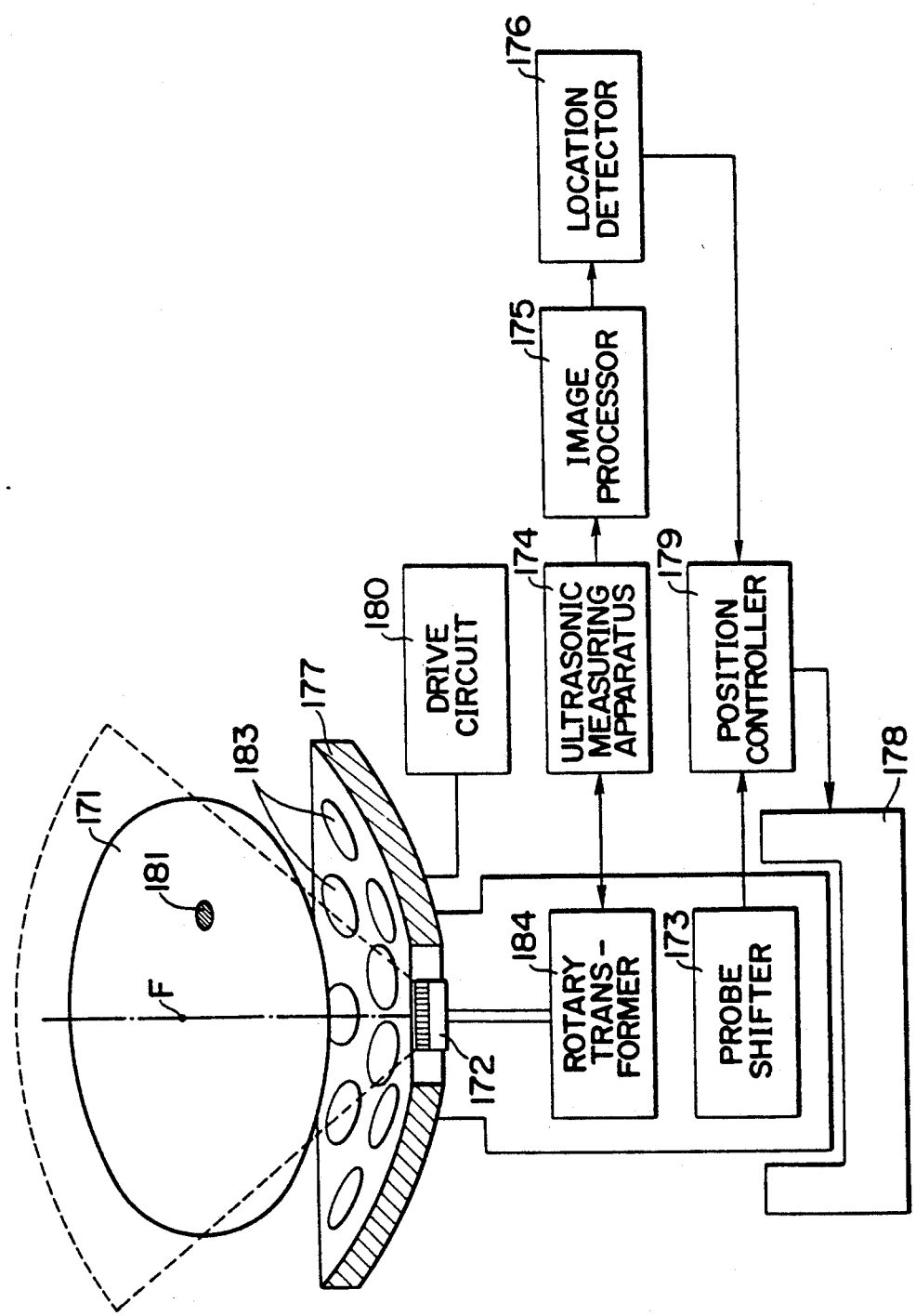
FIG. 30 is a schematic illustration of an ultrasonic therapeutical apparatus according to a sixteenth embodiment of the invention.

FIG. 30 shows an ultrasonic therepeutical apparatus according to a sixteenth embodiment of the invention which is designed to provide a three-dimensional scan by an ultrasonic probe to acquire a plurality of two-dimensional tomographic images, representing sections of the physical body of a patient, which are then processed in real time to locate the calculus, positional information of which is utilized for focussing an ultrasonic wave.

In FIG. 30, an array 177 of ultrasonic vibrators or piezoelectric elements 183 which are disposed along a apherical surface in a mosaic pattern is driven by a drive circuit 180 to develop an ultrasonic wave of an increased intensity, which is focussed upon a focus F of the array 177. An ultrasonic probe 172 of electronic sector scan type is used to derive a tomographic image of a sector-shaped area encompassed by broken lines.

The space between the patient 171 and the probe 172 is filled with a medium such as water in order to prevent an attenuation of the ultrasonic wave. Alternatively, a water bag, not shown, which is filled with water may be disposed in close contact with the patient 171 while covering the array 177. The probe 172 is driven in an angular increment of 45°, for example, by an ultrasonic scanner 173 which may comprise a stepping motor, and at each angular position, an ultrasonic measuring apparatus 174 delivers an ultrasonic transmit pulse which is fed through a rotary transformer 184. An echo signal from the probe 172 is fed back to the measuring apparatus 174 through the transformer 184 to display a B-mode image. A video signal from the apparatus 174 is fed to an image processor 175, which cooperates with a location detector 176 to obtain information representing the location of a calculus 181, with such information being fed to a position controller 179. Information representing the angle of rotation of the stepping motor is supplied from the scanner 173 to the position controller 179, which then activates the array shifting unit 178 on the basis of such information.

Figure 31:
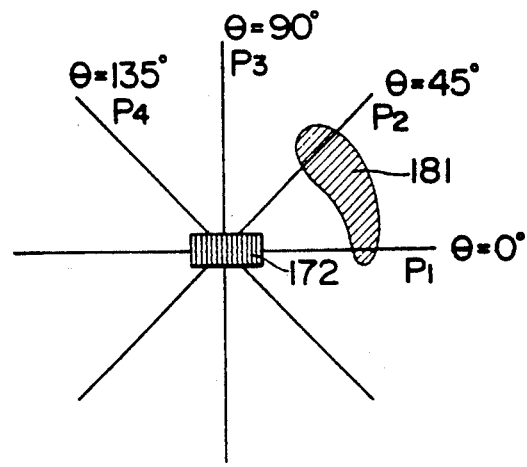
FIG. 31 is a diagram shown one example of angle of rotation of an ultrasonic probe used in the apparatus of FIG. 30.
Figure 32:
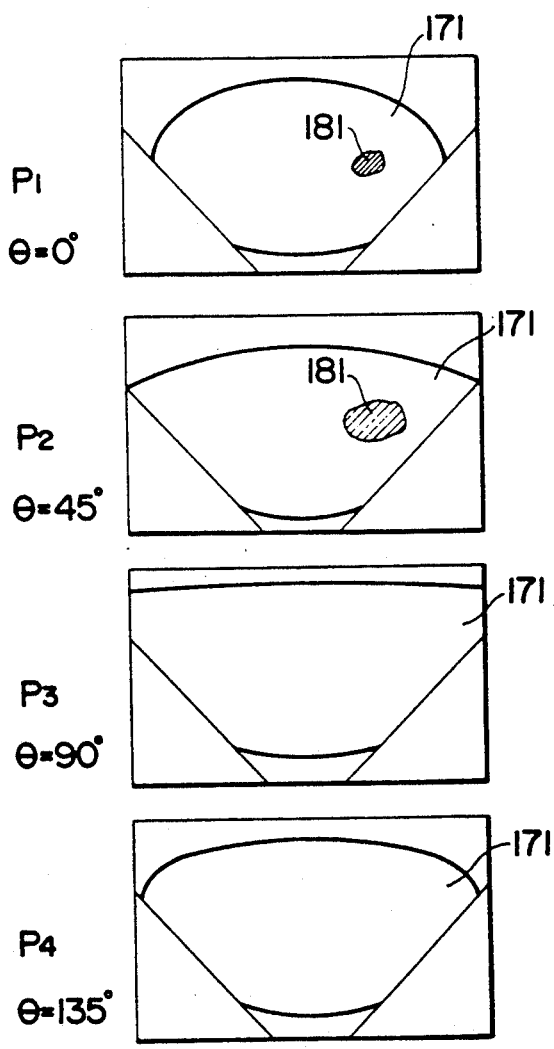
FIG. 32 illustrates several B-mode images at different angles of rotation of the probe.
Figure 33:
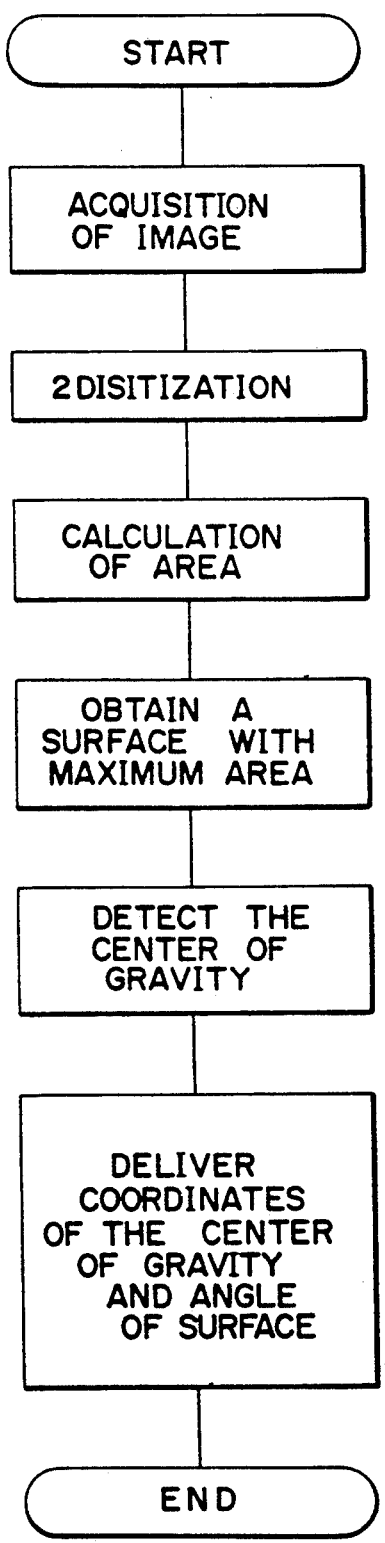
FIG. 33 is a flowchart illustrating a procedure which is utilized in ultrasonic therapeutical apparatus of the sixteenth embodiment to bring a calculus into the focal position of an array of vibrators.
Figure 34:
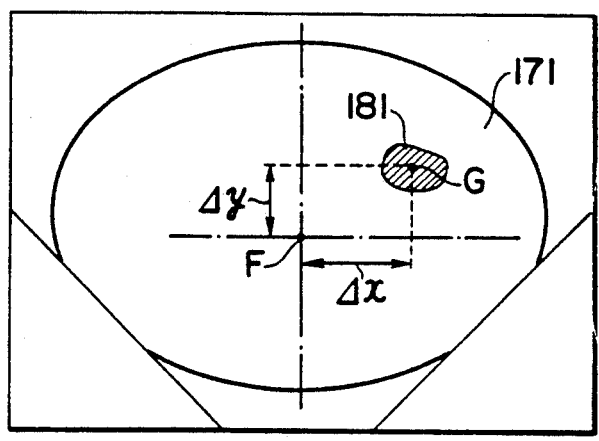
FIG. 34 illustrates a B-mode image, specifically showing the relationship between a calculus and the focal position of an array of ultrasonic vibrators on a P2 image plane shown in FIG. 32.

In operation, the probe scanner 173 rotates the probe 172 through angular increments so as to provide a B-mode image at each angular position which may correspond to an angular increment of 45°, for example, as illustrated in FIG. 31. By extracting areas of the image which exceeds a given threshold in strength, there are obtained four images P1 to P4 as indicated in FIG. 32. The combination of the image processor 175 and the location detector 176 operate upon each of these images P1 to P4 according to an algorithm indicated in FIG. 33. In this manner, information representing the B-mode image from the measuring apparatus 174 is acquired and stored in the image processor 175. Digitization may be performed to extract signal portions which exceed a given threshold, thereby facilitating the extraction of an echo which exibits a greater strength than the remaining tissues. The echo area over such extracted portions of the calculus 181 is then calculated. One of the four images P1 to P4 which exhibits a greatest area extracted for the calculus, which is the image P2 in the present example, is then determined. A corresponding angle of the scanner 173 (which is equal to 45° in this example) is determined. The location of the center of gravity G of the calculus represented by the echo in this plane is then determined (see FIG. 34), thus delivering the coordinates of the center of gravity G.

The location detector 176 then determines deviations $\Delta x$ and $\Delta y$ (see FIG. 34) of the center of gravity G from the focus F of the array 177 as well as the corresponding angle $\theta$ (see FIG. 31) of the probe scanner 173, delivering such information to the position controller 179. In response to information representing $\Delta x$ and $\Delta y$ and $\theta$, the position controller 179 drives the array shifting unit 178 which may comprise an X-Y-Z stage, for example, thus bringing the focal position F of the array 177 into coincidence with the location of the calculus 181 (see FIG. 30). Under this condition, the drive circuit 180 drives the array 177, causing the latter to emit an ultrasonic wave of an increased intensity which is concentrated upon the calculus situated at the focus F, thus fracturing it.

In the described embodiment, the B-mode image is acquired for each rotation of the probe through an angular increment of 45°, but it should be understood that the angular increment is not limited to this value, but that a smaller angular increment may be chosen to achieve a positional adjustment with a higher accuracy. For example, by driving the probe scan 173 at a rate of two revolutions per second and acquiring the image at an angular increment $\theta$ of 5°, thirty-eight B-mode images over an angular range of 360° may be processed within a time interval of 0.5 second, which is sufficient for tracking a movement of the calculus for practical purposes. In this manner, it is assured that the focus F of ultrasonic wave is maintained at the center of gravity of the calculus which is represented by the echo, thus assuring a maximum efficiency to fracture the calculus whenever the drive circuit 180 is energized.

Figure 35:
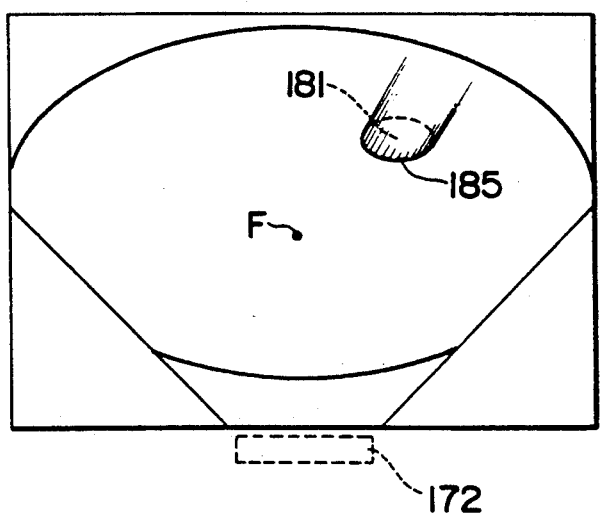
FIG. 35 shows a B-mode image, illustrating another use of the apparatus shown in FIG. 30.

FIG. 35 illustrates a mode image illustrating another use of the therapeutical apparatus shown in FIG. 30. It is assumed in the embodiment of FIG. 30 that the center of gravity of the echo representing a calculus coincides with the actual center of gravity of the calculus. However, with a calculus which exhibits an increased hardness, the nature of the ultrasonic wave may cause an echo 185 of an increased magnitude to be developed at its boundary of a calculus 181 located toward the probe 172 while failing to provide any echo for the remainder. In such instance, a calculation of the location of the center of gravity of the echo may result in a departure from the actual center of gravity of the calculus 181. To accommodate for such situation, the actual location of the calculus may be inferred from a point nearest the probe 172 or from a configuration of the echo for purpose of a focussing operation.

The probe 172 described above is of an electronic sector type, but is should be understood that a probe of a convex, linear or mechanical scan type may be used instead. Also, while the embodiment has been described in connection with fracturing a calculus, it should be understood that the technique of focussing an ultrasonic wave of an increased intensity according to the invention is also applicable to dissolution of thrombus, a progressively releasing agent (an ultrasonic wave is externally irradiated upon a mass of material in which a medicine is impregnated to cause a progressive release of the latter), hyperthermia or the like.

Figure 36:
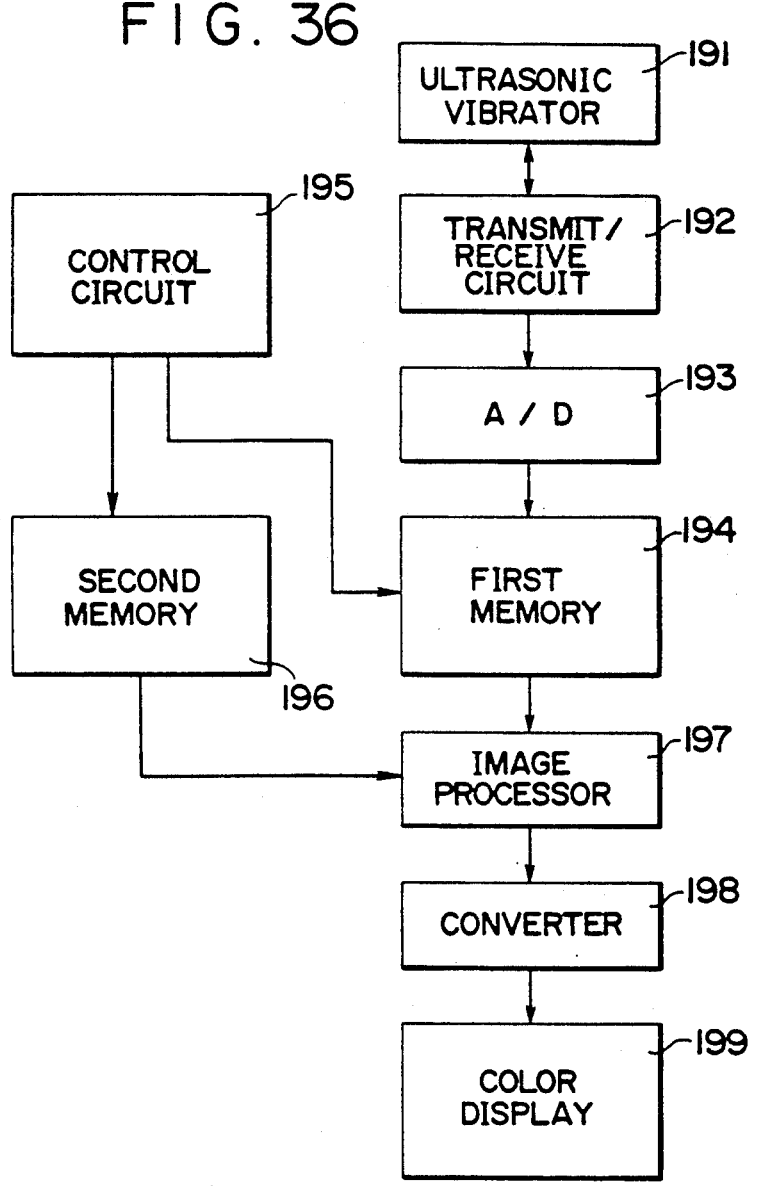
FIG. 36 is a block diagram of display means used in a calculus fracture apparatus of extracorporeal type according to a seventeenth embodiment of the invention.

FIG. 36 illustrates means for displaying an image which is obtained from a calculus fracturing apparatus of extracorporeal type constructed according to a seventeenth embodiment of the invention and which is utilized during the positioning of a calculus into coincidence with a focal position of a fracturing shock wave. In this Figure, an ultrasonic vibrator 191 is driven by a transmit/receive circuit 192 in order to detect the spatial location of a calculus situated within the physical body of a patient. An ultrasonic echo signal received by the transmit/receive circuit 192 is fed through an A/D converter 193, where analog-to-digital conversion is made, to a first memory 194 which stores ultrasonic image data.

On the other hand, data representing the distribution of intensity of a shock wave from a shock wave generator, not shown, is previously calculated and is stored in a second memory 196 which also defines an image memory. The both memories 194, 196 are controlled by a control circuit 195, which effects inputting image data from the respective memories into an image processor 197 where the both data are synthesized. Specifically, based on the data representing the distribution of intensity of a shock wave which is supplied from the second memory 196, the image processor 197 allocates colors to the image depending on the intensity of the shock wave, and such color distribution signal is superimposed upon data representing an ultrasonic tomographic image which is supplied from the first memory 194. The superimposed signal is converted into a standard television form by a standard television signal converter 198 before it is fed to a color display unit 199, which displays the resulting image.

Figure 37:
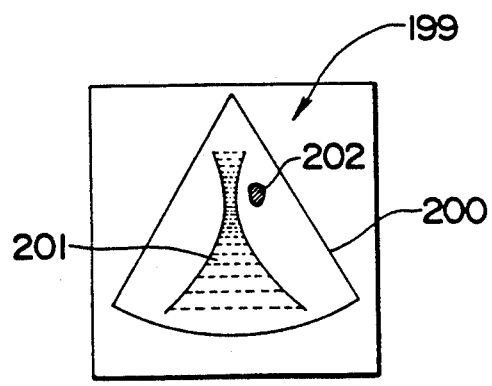
FIG. 37 is a diagram illustrating a data screen of the display.

FIG. 37 shows what is displayed on the screen of the color display unit 199. It will be noted that an ultrasonic tomographic image 200 and an image 201 representing the distribution of intensity of a shock wave are both superimposed upon each other on the screen. Since the image 201 is displayed in colors in superposition with the tomographic image 200, it is a simple matter to determine the location within the living body where the shock wave is applied and what the intensity of the shock wave is. This facilitates and assures that the calculus B be positioned at the location of the maximum intensity of the shock wave. It is also easily determinable whether organs such as a lung, intestines or bones which are sensitive to a shock wave are close enough to cause a risk of their damage, thus enabling any damage to these organs to be prevented.

It is possible in this embodiment that ultrasonic vibrators be located at positions which are displaced 90° from each other so that the resulting tomographic images may be superimposed upon the distribution of intensity of the respective shock waves on the screen of the color display unit 199.

Figure 38:
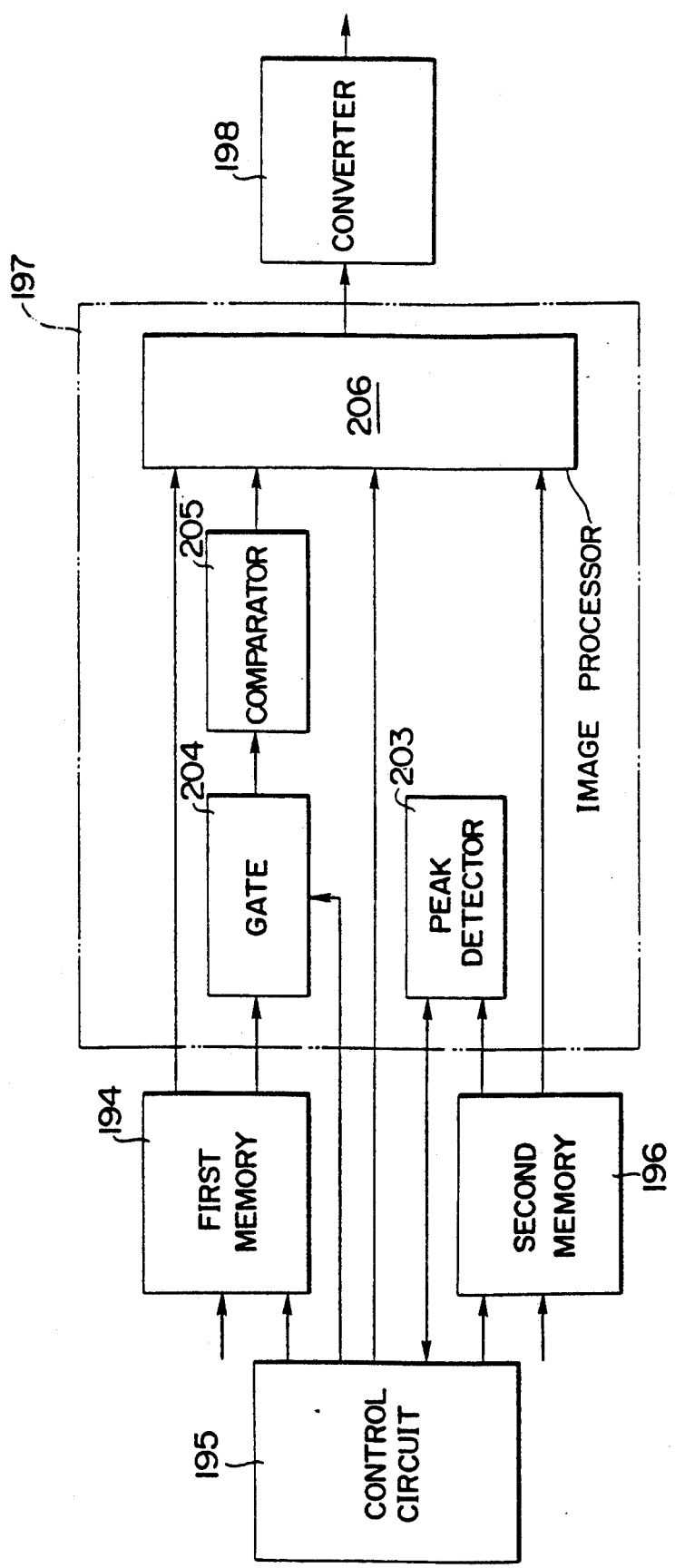
FIG. 38 is a block diagram of another form of display means.

FIG. 38 illustrates another form of image display means used in accordance with the invention. In this embodiment, a coincidence of a calculus 202 with the point of maximum intensity of the shock wave is indicated by a change in the display within an image processor 197. FIG. 38 only shows the internal construction of the image processor 197, with the remaining construction being similar to that of FIG. 36. Specifically, a tomographic data stored in a first memory 194 and data representing the distribution of intensity of a shock wave which is previously calculated and which is stored in a second memory 196 are fed to the image processor 197. Data representing the distribution of intensity of the shock wave is fed to a peak detector 203 where data having a maximum intensity is detected. An address corresponding to such data is fed to a control circuit 195 and thence to a gate 204. Data representing tomographic image which is supplied from the first memory 194 is passed through the gate, an output of which is fed to a comparator 205. Based on the recognition that the acoustical impedance of a calculus greatly deviate from the acoustical impedance of a living body to thereby allow the calculus to appear as an echo signal of an increased magnitude, a threshold of the comparator 105 is chosen to permit only the calculus to be detected. When a signal exceeding the threshold or a picture signal of the calculus is supplied to the comparator 205, the color which is allocated to the tomographic image of the calculus is changed. An image processor 206 combines a signal representing the tomographic image from the first memory 194, an output from the comparator 205 and data representing the distribution of intensity of the shock wave which is supplied from the second memory 196 together, and the combined signal is fed to a standard television signal converter 198 in order to permit it to be displayed on a color display unit 199. In this embodiment, when the calculus is positioned to a point of a maximum intensity of the shock wave, there occurs a change in the color of the calculus, thereby assuring a reliable positioning thereof.

Figure 39:
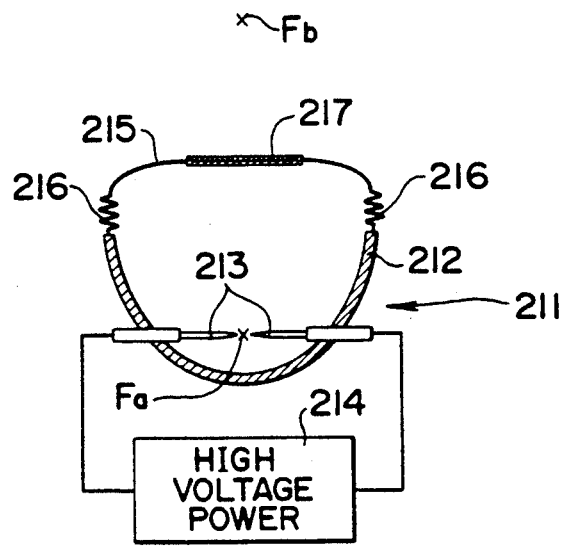
FIG. 39 is a longitudinal section of an ultrasonic probe and a shock wave generator which are used in a therapeutical apparatus of extracorporeal type according to a eighteenth embodiment of the invention.
Figure 40:
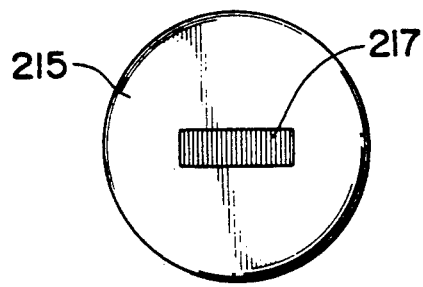
FIG. 40 is a plan view of the probe shown in FIG. 39.
Figure 41:
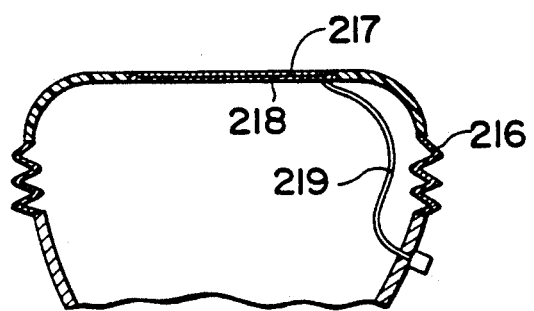
FIG. 41 is a fragmentary longitudinal section, to an enlarged scale, of the probe shown in FIG. 39.

FIG. 39 shows a therapeutical apparatus of extracorporeal type according to an eighteenth embodiment of the invention, specifically showing an ultrasonic probe and a shock wave generator of an ultrasonic observation apparatus as well as a water bag in longitudinal section. FIG. 40 shows the generator and the water bag in plan view, and FIG. 41 is a longitudinal section, to an enlarged scale, of a top portion of FIG. 39. In this embodiment, a shock wave generator of high discharged type is used to generate a shock wave which is used for fracturing a calculus. Specifically, the shock wave generator 211 comprises a paraboroidal metal plate 212, high tension discharged electrodes 213 and a high tension source 214. A water bag 215 formed by a thin film is connected to the metal plate through bellows 216 which are connected to the upper edge of the metal plate 212, thus covering the top surface of the metal plate. An ultrasonic probe 217 comprising an array of ultrasonic vibrators is secured to the upper surface of the water bag 215 with a carried member 218 (see FIG.

41) interposed therebetween. It is to be understood that the probe 217 is connected through a lead wire 219 to a measuring apparatus, not shown. The discharged electrodes 213 are spaced apart, with the gap therebetween being centered about one of the foci, Fa, of the paraboroidal plate 212, and the shock wave is focussed upon the other focus Fb where a calculus or the like may be located to achieve an efficient fracturing thereof.

The water bag 215 comprises a bag of a material such as Goatex (trademark) which is permeable to a gas such as air, but which is impermeable to a liquid such as water. The bag 215 is internally filled with shock wave transmitting medium such as water, and is formed to be deformable. It also includes means for injecting a liquid and means for controlling a pressure thereof. The probe 217 is of thin type such as may be formed by a piezoelectric film comprising PVDV (polyvinylidene fluoride), for example. It is applied to the surface of the water bag 215 to effect a linear or a sector scan.

In operation, the surface of the water bag 215 is applied to the surface of the physical body of a patient in a region opposite to an affected area, and the probe 217 is utilized to scan the affected area in order to detected the location of a calculus or the like. Subsequently, the shock wave generator 211 is operated upon to bring the focus Fb of the paraboroidal plate 212 into coincidence with the location of the calculus. A high tension discharged then takes place between the electrodes 213. Thereupon, a resulting shock wave is focussed upon the calculus which is located at the focus Fb, whereby the calculus is efficiently fractured.

Since the measuring unit which comprises the ultrasonic probe 217 is held in close contact with the surface of the physical body of the patient, the distance to the affected area can be minimized to assure the accuracy of a measurement and to facilitate a reliable detection of the calculus. Where a piezoelectric film such as comprising PVDV mentioned above is used, a high ultrasonic frequency can be used to improve the resolution over a probe comprising a conventional piezoelectric vibrator such as formed from ceramics. This enables a higher precision of detection. The carried member 218 which supports the probe 217 may be simply placed on the surface of the water bag 215, thus simplifying the arrangement and reducing the cost required.

Figure 42:
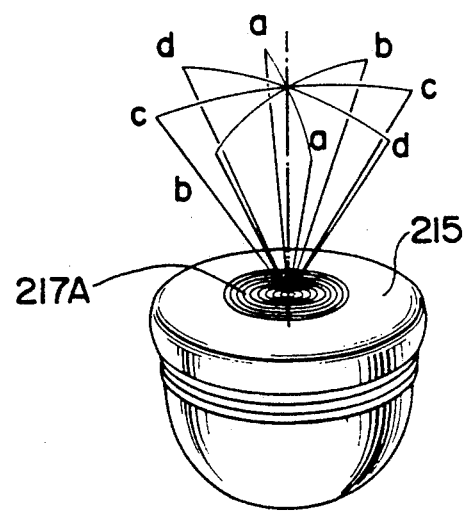
FIGS. 42 and 43 are a perspective view and a plan view of another form of probe.
Figure 43:
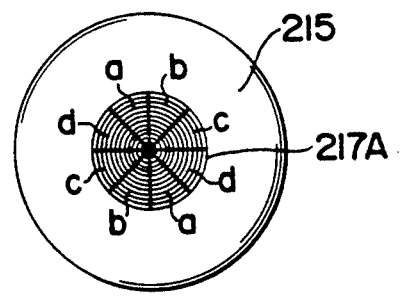
Figure 44:
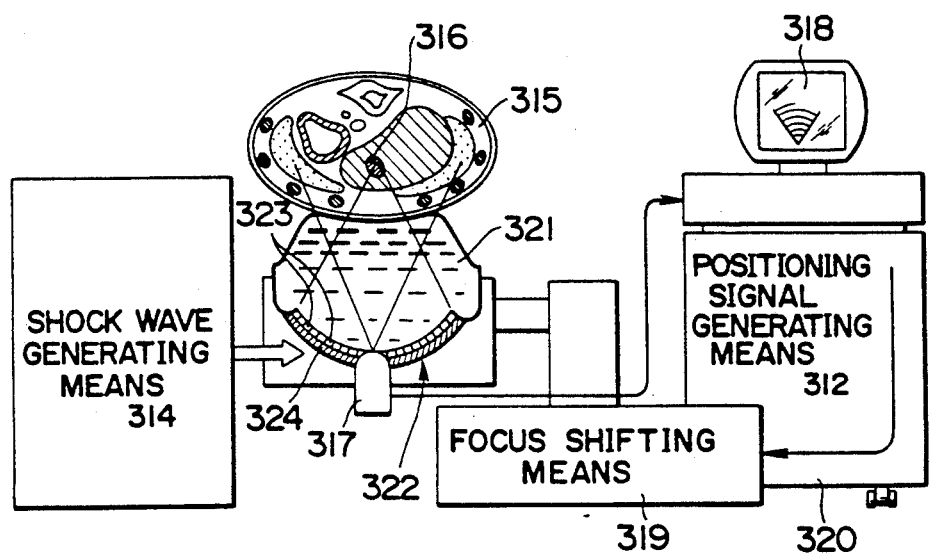
FIG. 44 is a schematic illustration of one conventional ultrasonic therapeutical apparatus of extracorporeal type.
Figure 45:
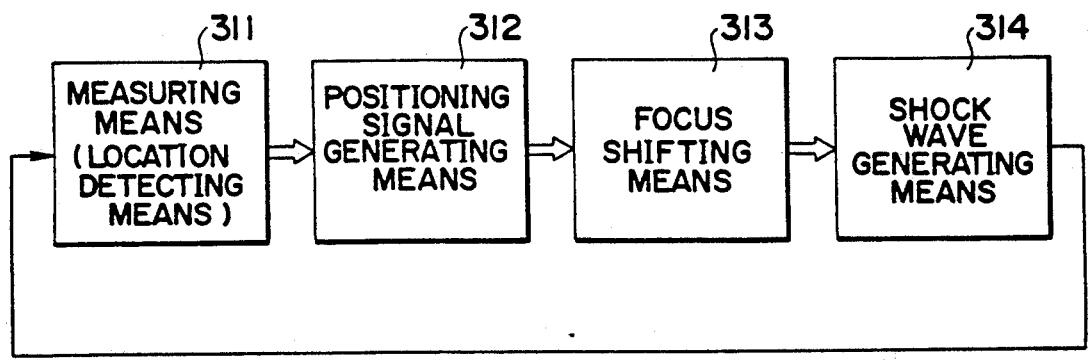
FIG. 45 is a block diagram illustrating the sequence of operation of the apparatus shown in FIG. 44.
Figure 46:
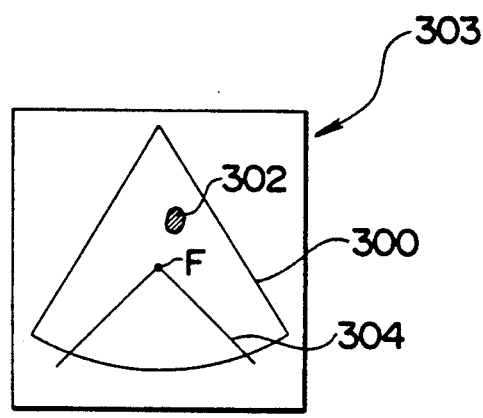
FIG. 46 is a diagram illustrating conventional data display screen.

In the described embodiment, the probe 217 comprises a linear array, but other arrangements of ultrasonic vibrators may also be used as illustrated in FIGS. 42 and 43. Specifically, an ultrasonic probe 217A of piezoelectric film type includes piezoelectric elements disposed in concentric circles and a plurality of tomographic images may be obtained by scanning in different directions which represent an equal division of the circumference such as a-a, b-b, c-c and d-d directions. In this manner, the location of the calculus can be easily and accurately determined. The ultrasonic generator of a high tension discharge type has been used in the described embodiment, but it should be understood that an ultrasonic shock wave generator comprising piezoelectric elements may be also used.

What is claimed is:

1. An extracorporeal therapeutic apparatus, comprising:
    a shock wave generator having a nominal focal point and being adjustable over a range of focal points, said nominal focal point being located in the middle of said range;
    human assisted location means for adjusting the relative position of said shock wave generator and a patient to be treated by said apparatus so that said shock wave generator is positioned at a location at which said nominal focal point corresponds with the initial position of a target within said patient;
    automatic tracking means for tracking subsequent movement of said target from said nominal focal point and for generating an output signal indicative of said subsequent movement of said target; and
    focusing means for adjusting the effective focal point of said shock wave generator as a function of said output signal to cause said effective focal point to coincide with the actual location of said target.

2. An extracorporeal therapeutic apparatus in accordance with claim 1, wherein:
    said shock wave generator comprises a plurality of ultrasonic vibrators each of which generates a respective shock wave when it is enabled, the location of said ultrasonic vibrators causing said respective shock waves to focus upon said nominal focal point when all of said ultrasonic vibrators are enabled simultaneously; and
    said focusing means adjusts said effective focal point by controlling the timing at which each of said ultrasonic vibrators is enabled.

3. A method for focusing a shock wave generated by a shock wave generator having a nominal focal point upon a target within a patient and being adjustable over a range of focal points, said nominal focal point being located in the middle of said range, said method comprising the steps of:
    adjusting, with the aid of a human operator, the initial position of said shock wave generator relative to a patient to be treated, so that said shock wave generator is positioned at a location at which said nominal focal point coincides with the initial position of a target within said patient;
    automatically tracking the subsequent movement of said target from said nominal focal point and generating an output signal indicative of said subsequent movement of said target; and
    automatically adjusting the effective focal point of said shock wave generator as a function of said output signal to cause said effective focal point of said shock wave generator to coincide with said actual location of said target.

* * * * *